United States Patent [19]
Gandolfi et al.

[11] 4,089,896
[45] May 16, 1978

[54] 8,12-DIISOPROSTANOIC ACID DERIVATIVES

[75] Inventors: Carmelo Gandolfi; Gianfederico Doria, both of Milan; Pietro Gaio, Belluno, all of Italy

[73] Assignee: Carlo Erba S.p.A., Milan, Italy

[21] Appl. No.: 315,460

[22] Filed: Dec. 15, 1972

[30] Foreign Application Priority Data

Dec. 17, 1971 Italy ............................... 32520 A/71

[51] Int. Cl.$^2$ .................... C07C 177/00; A61K 31/19; A61K 31/215
[52] U.S. Cl. ......................... 260/514 D; 260/343.3 P; 260/346.22; 260/456 R; 260/456 P; 260/501.17; 260/501.18; 260/520 B; 424/305; 424/317; 542/426; 560/121; 560/231
[58] Field of Search ...................... 260/468 D, 514 D

[56] References Cited

FOREIGN PATENT DOCUMENTS 2,345,695   9/1973   Germany .............................. 260/468

OTHER PUBLICATIONS

Corey et al. I, J. Org. Chem. 37, 3043, (1972).
Corey et al. II, JACS 92, 387 (1970).

*Primary Examiner*—Robert Gerstl
*Attorney, Agent, or Firm*—Murray & Whisenhunt

[57] ABSTRACT

Optically active 8,12-diisoprostanoic acids and derivatives, processes for making same, pharmaceutical compositions containing same, and intermediates for producing same are disclosed. The acids include, for instance, 5c,13t-11α,15S-dihydroxy-9-oxo-8,12-diisoprostadienoic acid.

The compounds of the present invention can be used in the same uses as the natural prostaglandins, including the treatment of asthma, parturition to facilitate child bearing labor and as abortion agents.

13 Claims, No Drawings

8,12-DIISOPROSTANOIC ACID DERIVATIVES

This invention relates to optically active 8,12-diisoprostanoic acid derivatives, to processes for making them, to pharmaceutical compositions containing them and to novel intermediates useful in the processes.

The natural prostaglandins are C-20 unsaturated, non-aromatic fatty hydroxylic carboxylic acids in which $C_8$ and $C_{12}$ are linked to form a five-membered ring. The basic carbon skeleton of prostanoic acid has the following structure:

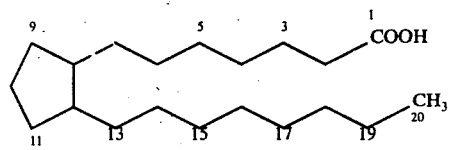

In the body, prostaglandins are synthesized from C-20 essential fatty acids by a microsomal enzymatic systems. The natural prostaglandins are known to have various physiological properties, i.e. hypertensive, hypotensive and smooth muscle stimulating activity. They also inhibit and reverse blood platelet adhesiveness and aggregation, which is the initial stage of thrombosis. In general, the effects of prostaglandins are based on regulating the activity of smooth muscle, blood flow and secretion (including some endocrine gland secretions). Through these actions, they are able to affect many aspects of human physiology: in particular, they can be useful in the prevention of peptic ulcers, asthmatic access, hypertension, nasal congestion, as agents for abortion, as agents for inducing menstruation and the impediment of the implantation of a fertilized ovum, and furthermore prostaglandins have been used in parturition to facilitate childbearing labour. Natural prostaglandins are, however, rapidly converted in the body to pharmacologically inactive metabolites; their short half life (about 10 min.) is a hindrance to the use of natural prostaglandins as therapeutic agents.

Dehydrogenation of the allylic hydroxy function at C-15 which is present in all the naturally occurring prostaglandins, by 15-hydroxy-prostaglandin dehydrogenases (NAD-dependent enzymes), is the first and more important metabolic step.

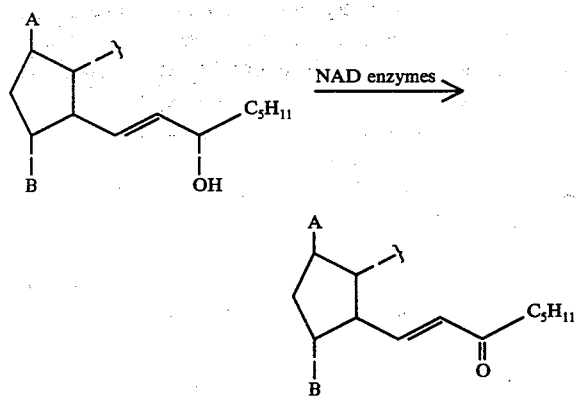

This first degradation step, involving the conversion into $\Delta^{13(14)}$-15-keto prostaglandins, decreases the biological activity of prostaglandins to one tenth or less, and therefore quite probably represents one of the crucial factors governing the physiological and pharmacological effects of prostaglandins. Consequently, molecular modifications which reduce the rate of this metabolic process should give rise to favourable effects on the other biological parameters. Ramwell et al., Nature, 1969, 221, 1251, and Shio et al., Experientia. 1970, 26, 355 recognized that rac-11,15-epi-$PGE_1$ is two to ten times as active as rac-$PGE_1$ as a consequence of the decreased degradation rate of the enantio-11,15-epi-$PGE_1$.

On the other hand, partially resolved ent-11,15-epi-$PGE_1$ (optical activity about 35%) was found to be at least as potent as nat-$PGE_1$ on rat uterus and far more potent on the other tissue preparations, and its degradation rate has been reckoned to be only about 15% of the rate of the nat-$PGE_1$. (Shio et al., loc. cit.)

The invention provides pure optically active 8,12-diisoprostanoic acid derivatives (also named entprostaglandins), e.g. ent-11,15-epi-PGE ($E_1$ and $E_2$) and ent-11,15-epi-PGF ($F_{1\alpha}$, $F_{1\beta}$, $F_{2\alpha}$, $F_{2\beta}$), as well as related synthetic derivatives thereof, all of which have a reduced metabolic degradation rate compared to natural prostaglandins, thus allowing an efficient therapeutic action at lower dosages. The 8,12-diisoprostanoic acid derivatives of this invention can be used in the same applications as the natural prostaglandins discussed hereinbefore. In particular, the 9-keto derivatives are especially active in the treatment of asthma and in parturition to facilitate childbearing labour, while the 9-hydroxy derivatives are especially useful as agents for abortion and in parturition to facilitate chilbearing labour.

The compounds of the invention have the general formulas (I)

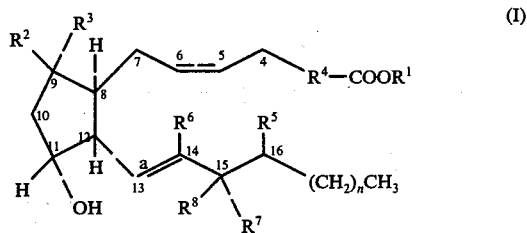

and (II)

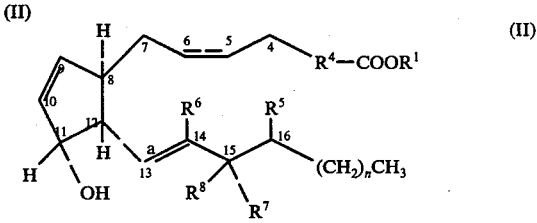

wherein $R^1$ is a hydrogen atom, a cation of a pharmaceutically acceptable base or a $C_{1-12}$ alkyl group; one of $R^2$ and $R^3$ is a hydrogen atom and the other is a hydroxy group or $R^2$ and $R^3$ together form an oxo group; the symbol ═══ represents a single or cis-double bond; $R^4$ is —$CH_2CH_2$—, —$OCH_2$-, —$SCH_2$—, cis—CH═CH—, trans—CH═CH— or —C≡C—; n is 3 or 4; $R^5$ and $R^6$, which may be the same or different, is a hydrogen atom or a $C_{1-14}$ alkyl group; one of $R^7$ and $R^8$ is a hydrogen atom and the other is a hydroxy group; and double bond a is a trans-double bond.

The broken lines in the formulae of this specification indicate that the substituents are in the $\alpha$-configuration, i.e. are below the plane of the ring.

Preferred compounds are those of general formula (I), wherein preferably R⁴ is —CH₂—CH₂— or —OCH₂— and R⁶ is a hydrogen atom. Examples of the preferred compounds are:

5c,13t-11α,15S-dihydroxy-9-oxo-8,12-diisoprostadienoic acid;
5c,13t-11α,15R-dihydroxy-9-oxo-8,12-diisoprostadienoic acid;
13t-11α,15S-dihydroxy-9-oxo-8,12-diisoprostenoic acid;
13t-11α,15R-dihydroxy-9-oxo-8,12-diisoprostenoic acid;
5c,13t-9β,11α,15S-trihydroxy-8,12-diisoprostadienoic acid;
5c,13t-9α,11α,15S-trihydroxy-8,12-diisoprostadienoic acid;
5c,13t-9β,11α,15R-trihydroxy-8,12-diisoprostadienoic acid;
5c,13t-9α,11α,15R-trihydroxy-8,12-diisoprostadienoic acid;
5c,13t-9β,11α,15S-trihydroxy-3-oxa-8,12-diisoprostadienoic acid;
5c,13t-9β,11α,15R-trihydroxy-3-oxa-8,12-diisoprotadienoic acid;
5c,13t-9β,11α,15S-trihydroxy-ω-homo-8,12-diisoprostadienoic acid;
5c,13t-11α,15S-dihydroxy-9-oxo-ω-homo-8,12-diisoprostadienoic acid;
5c,13t-11α,15S-dihydroxy-9-oxo-3-oxa-8,12-diisoprostadienoic acid;
5c,13t,11α,15S-dihydroxy-9-oxo-16-methyl-3-oxa-8,12-diisoprostadienoic acid;
5c,13t-11α,15S-dihydroxy-9-oxo-16-methyl-8,12-diisoprostadienoic acid;
5c,13t-9α,11α,15S-trihydroxy-ω-homo-8,12-diisoprostadienoic acid;
5c,13t-9α,11α,15S-trihydroxy-3-oxa-8,12-diisoprostadienoic acid;
5c,13t-9α,11α,15S-trihydroxy-16-methyl-8,12-diisoprostadienoic acid;
5c,13t-11α,15S-dihydroxy-8,12-diisoprosta-5,9,13-trienoic acid.

The ω-homo compounds are those wherein n is 4.

The compounds of general formulas (I) and (II) may be prepared by a process comprising reacting a compound of general formula (III)

(III)

wherein R⁵, R⁶, n and a are as defined above, one of $R_r^7$ and $R_x^8$ is a hydroxy or a known protecting group bound to the chain by an ethereal oxygen atom, and the other is a hydrogen atom, and Y is a hydroxy or a known protecting group as defined above, with a Wittig reagent comprising the group —CH₂CH₂—R⁴—COOR¹ wherein R⁴ is as defined in claim 1 and R¹ is a hydrogen atom or a C₁₋₁₂ alkyl group, to give a compound of general formula (IV)

(IV)

wherein the double bond in the 5,6-position is a cis double bond, and R¹, R⁴, R⁵, R⁶, $R_f^7$, $R_f^8$, Y, n and a are as defined above, optionally hydrogenating the compound of formula (IV) in the 5,6-position and then, when in the compound of general formula (IV) or in its hydrogenation product, Y is a known protecting group as defined above and/or one of $R_f^7$ and $R_f^8$ is a known protecting group as defined above and the other is a hydrogen atom, deetherifying the compound of formula (IV) or its hydrogenation product in the 11- and/or 15-position to give a compound of general formula (I), wherein R² is a hydroxy and R³ is a hydrogen atom, or alternatively (a) oxidizing the compound of general formula (IV), wherein Y is a known protecting group as defined above and one of $R_f^7$ and $R_f^8$ is a known protecting group as defined above and the other is a hydrogen atom, or its hydrogenation product, wherein Y, $R_f^7$ and $R_f^8$ have the same meanings, in the 9-position to give a compound of general formula (V)

(V)

wherein the symbol ≡≡≡, R¹, R⁴, R⁵, R⁶, n and a are as defined above, Y is a known protecting group as defined above and one of $R_f^7$ and $R_f^8$ is a known protecting group as defined above and the other is a hydrogen atom, which, in turn, may be either directly deetherified in the 11- and 15-positions to give a compound of general formula (I), wherein R² and R³ together form an oxo group, or reduced in the 9-position to give a mixture of the 9α- and 9β-ols having the general formulas (VI) and (VII)

(VI)

9α-ols

-continued

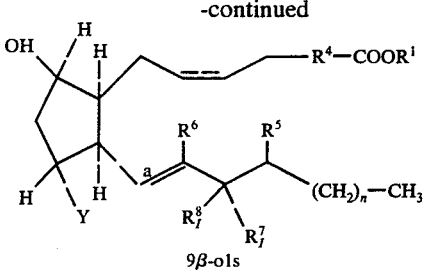

9β-ols (VII)

wherein the symbol ═══, $R^1$, $R^4$, $R^5$, $R^6$, n and a are as defined above, Y is a known protecting group as defined above and one of $R_I^7$ and $R_I^8$ is a known protecting group as defined above and other is a hydrogen atom, which mixture is then, in any order, separated and deetherified in the 11- and 15-positions, so obtaining a compound of general formula (I), wherein one of $R^2$ and $R^3$ is hydroxy and the other is hydrogen atom, (b) or reacting the compound of general formula (IV), wherein Y is a known protecting group as defined above and one of $R_I^7$ and $R_I^8$ is a known protecting group as defined above and the other is a hydrogen atom, or its hydrogenation product, wherein Y, $R_I^7$ and $R_I^8$ have the same meanings, with a compound of general formula $R^aSO_2X$ wherein $R^a$ is a substituted or unsubstituted alkyl or aryl group and X is a halogen atom, to give a compound of general formula (VIII)

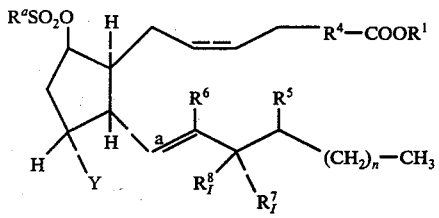

(VIII)

wherein the symbol ═══, $R^a$, $R^1$, $R^4$, $R^5$, $R^6$, n and a are as defined above, Y is a known protecting group as defined above and one of $R_I^7$ and $R_I^8$ is a known protecting group as defined above and the other is a hydrogen atom, which, by reaction with a carboxylic acid salt, yields a mixture of the compounds of formula (IX)

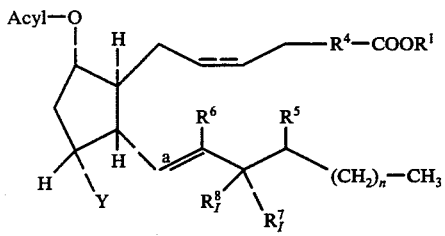

(IX)

and of formula (X)

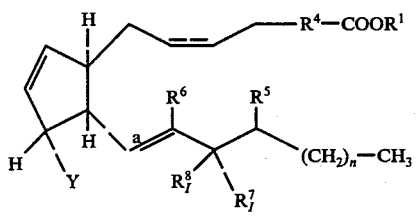

(X)

wherein the symbol ═══, $R^1$, $R^4$, $R^5$, $R^6$, n and a are as defined above, Y is a known protecting group as defined above and one of $R_I^7$ and $R_I^8$ is a known protecting group as defined above and the other is a hydrogen atom, which mixture is then, in any order, optionally selectively saponified, deetherified in the 11- and 15-positions and separated, so obtaining a compound of formula (I), wherein $R^3$ is hydroxy and $R^2$ is a hydrogen atom, and a compound of formula (II).

Compounds wherein $R^1$ is a hydrogen atom can be esterified or reacted with a pharmaceutically acceptable base to give compounds wherein $R^1$ is, respectively, a $C_{1-12}$ alkyl group or a cation of a pharmaceutically acceptable base. Compounds wherein $R^1$ is a $C_{1-12}$ alkyl group can be hydrolysed to give those wherein $R^1$ is a hydrogen atom.

The known protecting groups (i.e. ether groups) should be convertible to hydroxy groups under mild reaction conditions, e.g. acid hydrolysis. Examples are acetalic ethers, enolethers and silylethers. The preferred groups are

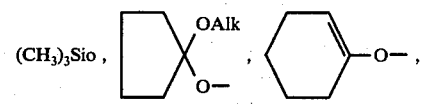

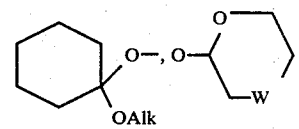

wherein W is —O— and —$CH_2$—, and Alk is a lower alkyl group.

In the compounds of general formula (III), the wavy line attachment ( $\int$ ) indicates that the hydroxy group is in the α-configuration, i.e. below the plane of the ring, or in the β-configuration, i.e. above the plane of the ring.

The Wittig reaction is suitably carried out using at least one mole, preferably 2-10 moles, of the Wittig reagent per mole of lactol.

The reaction is generally performed in an organic solvent, for example ether, benzene, toluene, hexane, dimethylsulphoxide, tetrahydrofuran, methylene chloride and chloroform, in presence of a base, preferably sodium hydride and potassium tert.-butoxide, at 0° C to the reflux temperature of the reaction mixture, preferably at room temperature or below. The reaction can take a few hours to several days depending on the temperature and concentration of the reaction mixture and the specific Wittig reagent used.

The term "Wittig reagent" includes compounds of general formula

wherein Hal is bromo or chloro and $R^1$ and $R^4$ are as defined above. Other phosphorus derivatives, e.g. the diethyl derivatives, are also included. The preparation of these reagents is discussed in detail by Tripett, Quart. Rev. 1963 XVII, No. 4, 406.

The double bond in the 5(6) position which is a cis bond, can be selectively reduced using a palladium-carbon catalyst at −20° C to −10° C, so that the double bond in the 13(14)-position is unaffected. Deetherification is performed under conditions of mild acid hydrolysis, for example with mono- or poly-carboxy acids e.g. formic, acetic, oxalic, citric and tartaric acid, and in a solvent, for example water, acetone, tetrahydrofuran, dimethoxyethane and lower aliphatic alcohols. Preferably, 0.1N to 0.25N polycarboxylic acid (e.g. oxalic or citric acid) is used in the presence of a convenient low boiling co-solvent which is miscible with water and which can be easily removed in vacuo at the end of the reaction.

The oxidation of the 9-hydroxy group to yield an oxo group may be carried out with for example, Jones reagent. The subsequent reduction of the keto group in the 9-position to give a mixture of the 9α-hydroxy and 9β-hydroxy-11-ethers may be performed for example by using sodium, lithium or zinc borohydride.

Separation of the 9α-hydroxy and 9β-hydroxy-11-ethers from each other and/or from the free 11,15-diols may be carried out for example by chromatographic techniques, preferably column chromatography.

The reaction with the sulphonic acid halide is suitably performed in presence of a base, for example pyridine, collidine or a trialkylamine. The subsequent nucleophilic substitution reaction can with a carboxylic acid salt be suitably carried out with a formic, acetic or propionic acid salt in a solvent, e.g. water, dimethylsulphoxide, dimethylformamide, hexamethyl phosphoric triamide, acetone and 2-butanone, and their mixtures, in presence or absence of the free acid.

The subsequent saponification, deetherification and separation of the mixture into its components may be performed in any order. Saponification is carried out, for example, by treatment with an alkali in an aliphatic alcohol,, preferably a low molecular weight alcohol; deetherification may be performed as described above under conditions of mild acid hydrolysis, for example with oxalic acid in acetone, while separation may be carried out by means of chromatographic techniques, preferably column chromatography, for example on acid washed silica. Saponification may if desired be selective, as stated above, in that according to the reaction conditions used, it can yield compounds wherein $R^1$ is a hydrogen atom or a $C_{1-12}$ alkyl group. For instance, saponification at the end of the chain does not occur when an alkali metal or carbonate or bicarbonate in anhydrous methanol is used.

The compounds of general formula (III) may be prepared in turn, by means of a multi-step process using as starting material a pure optically active compound of general formula (XI)

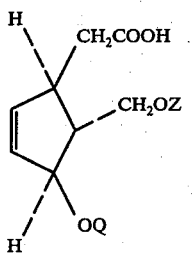

(XI)

wherein Z is a lower alkyl group, preferably methyl, or an unsubstituted or substituted aralkyl group, preferably benzyl or p-methoxybenzyl, and Q is a hydrogen atom or an aliphatic acyl group. The compound of formula (XI) may be prepared by crystallization with optically active bases and acylation by conventional methods, starting from the compound of general formula

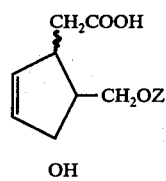

wherein Z is as defined above. This compound is a mixture of both optical antipodes (laevorotatory and dextrorotatory). Its preparation is described by Corey et al., J. Am. Chem. Soc., 1969 91, 5675; ibid. 1971, 93, 1489 and 1491 ibid., 1971, 93, 4326, who however use, in the total synthesis of the naturally occurring prostaglandins, only the dextrorotatory antipode having the absolute formula

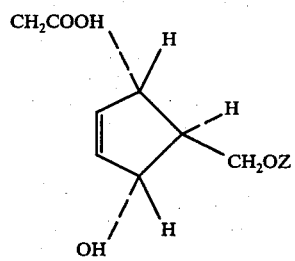

The starting material used in the present invention is the laevorotatory antipode having the absolute formula (XI). The multi-step process to obtain the compound of general formula (III) involves the following steps:

(1) Reaction of the compound of formula (XI), in the form of a salt with an alkali or alkaline earth metal or an optically active base, with an aqueous solution of potassium triiodide to give a compound of general formula (XII)

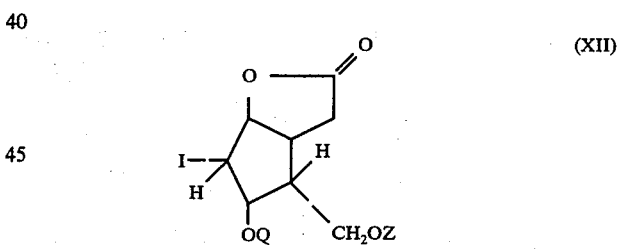

(XII)

wherein Z and Q are as defined above;

(2) Dehalogenation of the compound of formula (XII) to give a compound of formula (XIII)

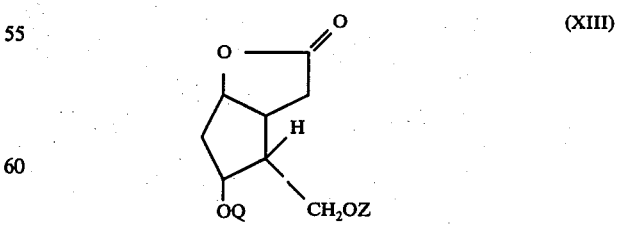

(XIII)

wherein Z and Q are as defined above; if Q is a hydrogen atom, the dehalogenation is preferably performed with a reducing agent, which is preferably tributyl tin hydride in benzene or chromous acetate in thioethanol and dimethylsulphoxide. If Q is an acyl group, the dehalogenation is preferably performed with sodium cyanoborohydride in hexamethylphosphoric triamide;

(3) Reaction of the compound of formula (XIII), after saponification if Q is an acyl group,, with a halide of formula $R^aSO_2X$, wherein X is a halogen atom and $R^a$ is an unsubstituted or substituted alkyl or aryl group, to give a compound of general formula (XIV)

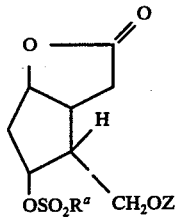

(XIV)

wherein $R^a$ and Z are as defined above; the reaction is suitably performed in presence of a base, preferably pyridine, an alkylpyridine or a trialkylamine;

(4) Reaction of a compound of formula (XIV) with an aliphatic carboxylic acid salt to give a compound of general formula (XV)

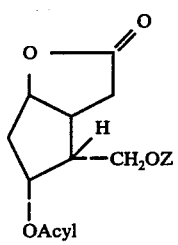

(XV)

wherein Z is as defined above; the carboxy acid is preferably formic, acetic or propionic acid and the reaction is preferably performed in a solvent, e.g. water, dimethylsulphoxide, dimethylformamide, hexamethyl phosphoric triamide, acetone or 2-butanone or their mixtures. The small amount of the $\Delta^{3(4)}$-lactone which is simultaneously obtained can be easily removed by fractional crystallization or column chromatography;

(5) Saponification to yield the 4-ol; the saponification may be performed by conventional methods using an alkali or acid;

(6) Esterification of the 4-ol with an aromatic carboxy acid. Esterification is preferably performed with p-phenylbenzoylchloride in pyridine. This esterification involves an aroyl group because the presence of such a group facilitates the subsequent oxidation to an aldehyde and yields a more easily crystallizable product;

(7) Deetherification of the compound thus obtaned to give a compound of general formula (XVI)

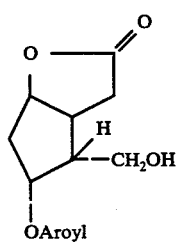

(XVI)

The deetherification is suitably performed using $BBr_3$, $BCl_3$, $(C_6H_5)_3C^+$ $ClO_4^-$, or $(C_6H_5)_3C^+$ $BF_4^-$ in a suitable solvent, for example methylene chloride, and for the benzyl ethers using reductive cleavage with hydrogen in presence of $PtO_2$ or palladium on carbon as catalyst;

(8) Oxidation of the compound of general formula (XVI) to yield the compounds of general formula (XVII)

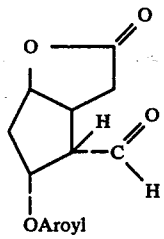

(XVII)

The oxidation may be performed for example in dimethyl sulphoxide using a carbodiimide, for example dicyclohexylcarbodiimide, in presence of a suitable protonating agent, e.g. orthophosphoric acid or pyridine trifluoroacetate, of if desired by means of a modified Collins reagent (Ratcliffe and Rodehorst, 1970, J. Org. Chem. 35, 4000);

(9) Reaction of the aldehyde with an alkali or alkaline earth metal salt of a compound of general formula (XVIII)

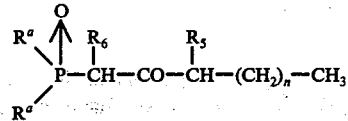

(XVIII)

wherein $R^5$, $R^6$ and n are as defined above, and each of the groups $R^a$, which may be the same or different is a lower alkyl group, to give a trans-enone of general formula (XIX)

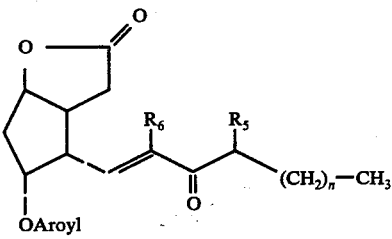

(XIX)

wherein $R^5$, $R^6$ and n are as defined above. The reaction is suitably performed in a solvent which is preferably dry dimethoxyethane, tetrahydrofuran or benzene or their mixtures, and using a suspension of an alkali or alkaline earth metal salt of the compound of general formula (XVIII) in this solvent. The compound of general formula (XVIII) may be prepared by reacting a phosphonate of the formula

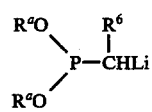

wherein $R^a$ and $R^6$ are as defined above, with an ester of formula

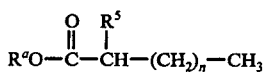

wherein $R^a$, $R^5$ and n are as defined above, according to Corey and Kwiatakowski, 1966, J. Amer. Chem. Soc., 88, 5654.

(10) Reducing of the 15-oxo group to yield a mixture of the 15S and 15R-ols having the formula (XIXa) and (XIXb)

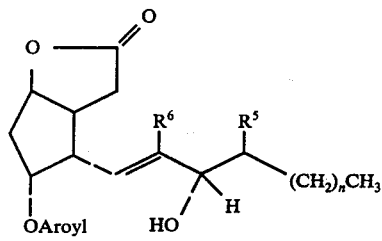

XIXa (15S-ol)

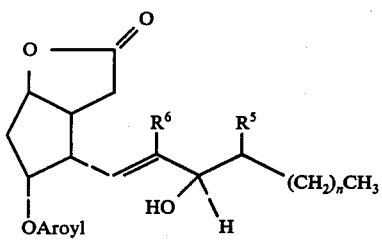

XIXb (15R-ol)

The reduction may be suitably performed in a solvent preferably acetone, ether, dimethoxyethane, dioxan or benzene or their mixtures, by using sodium, lithium or zinc borohydride;

(11) Separation of the 15S-ol from the 15R-ol; this may be performed by chromatography, preferably column chromatography, or fractional crystallization;

(12) Saponification by known methods to yield compounds having the following general formula (XX)

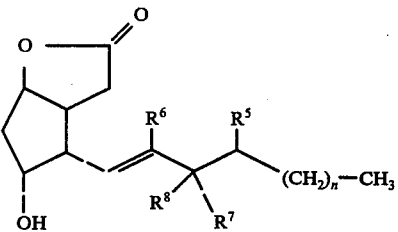

(XX)

wherein one of the group $R^7$ and $R^8$ is hydroxy and the other is a hydrogen atom, and $R^5$ and $R^6$ are as defined above;

(13) Etherification of the 11- and 15-hydroxy groups to give a compound of general formula $(X_{XI})$

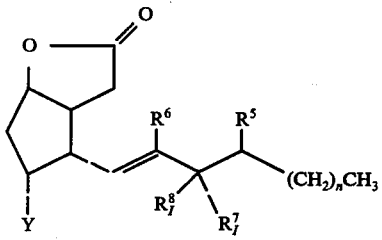

(XXI)

wherein Y and one of $R_f^7$ and $R_f^8$ are known protecting groups as defined above. The etherification is preferably carried out with a vinylic ether of formula

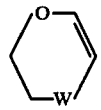

wherein W is —O— or —$CH_2$—, in presence of catalytic amounts of for example phosphorus oxychloride, p-toluenesulphonic acid or benzene sulphonic acid, or with a silyl ether, for instance by reacting a trisubstituted chlorosilane in presence of an acceptor base (for example, a trialkylamine) of the hydrogen halide formed, or with an enol ether, for instance by reaction, in presence of an acid catalyst, with a cyclopentanone or cyclohexanone diacetal, at the reflux temperature in an inert solvent, and distilling the alcohol formed to obtain mixed acetals or enol ethers, according to the quantity of catalyst used or the heating time;

(14) Reduction of the compounds of general formula (XXI) to yield the lactol derivatives of general formula (XXII)

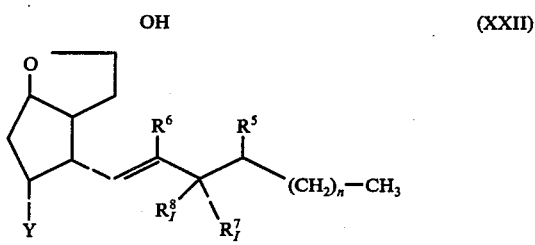

(XXII)

wherein Y, $R_f^7$ and $R_f^8$ are as defined above. The reduction may be performed by treatment with a disobutylaluminium hydride or sodium bis-(2-methoxyethoxy)aluminium hydride in an inert solvent, for example toluene, n-heptane, n-hexane or benzene or their mixtures, at below $-30°$ C;

(15) Optional deetherification of the compounds of general formula (XXII) to give compounds having the free 11- and 15-hydroxy groups; the deetherification may be accomplished by mild acid hydrolysis, in a solvent miscible with water, with a solution of a mono- or polycarboxylic acid.

Of the above intermediates, the following are compounds of the invention:

(a) a compound of general formula (XXIII)

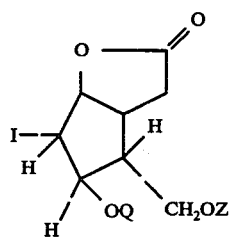

(XXIII)

wherein Q is a hydrogen atom or an aliphatic acyl group, and Z is a lower alkyl or substituted or unsubstituted aralkyl group.

(b) A compound of general formula (XXIV)

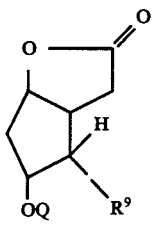

(XXIV)

wherein Q is an acyl group and R$^9$ is a hydroxymethyl or formyl group or a group of formula —CH$_2$OZ wherein Z is as defined above; preferably the acyl group is an arcyl or aliphatic acyl group or a group of formula —SO$_2$R$^a$ wherein R$^a$ is as defined above (c) A compound of general formula (XXV)

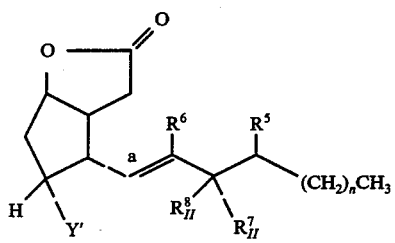

(XXV)

wherein R$^5$, R$^6$, n and a are as defined above, P is an oxo or hydroxy group, Y is a hydroxy or aroyl group or a known protecting group as defined above and one of R$_{II}^7$ and R$_{II}^8$ is a hydroxy or aroyl group or a known protecting group as defined above and the other is a hydrogen atom or R$_{II}^7$ and R$_{II}^8$ together form an oxo group.

The compounds of general formula (I) and (II) can be administered orally, parenterally or intravenously, by rectal suppositories or by inhalation. For example, they can be administered by intravenous infusion of a sterile isotonic saline solution at the rate of 0.01 to 10, preferably 0.05 to 1, micrograms/kilogram of mammal body weight per minute.

The invention therefore also provides a pharmaceutical composition comprising a compound of general formula (I) and (II) and a pharmaceutically acceptable carrier or diluent.

The compositions may be prepared by conventional methods and can be, for example, in the form of tablets, capsules, pills, suppositories or bougies, or in liquid form e.g. solutions, suspensions or emulsions.

Examples of substances which can serve as carriers or diluents are water, gelatin, lactose, starches, magnesium stearate, talc, vegetable oils, benzyl alcohols and cholesterol.

The invention is illustrated by the following Examples, wherein the abbreviations "THP", "DMSO" and "DIBA" refer to tetrahydropyranyl, dimethylsulphoxide and diisobutylaluminium hydride, respectively.

EXAMPLE 1 dl-5-Benzyloxymethyl-cyclopent-2-enyl-4-hydroxy-1-acetic acid (88.5 g.) in ether (1500 ml.) was slowly treated with dehydroabietylamine (92.4 g.) in ether (500 ml.). The precipitated salt (140 g., $[\alpha]_D^{MeOH} = + 19°$) was collected by filtration and was crystallised from benzene (20 ml./g.) to afford a salt (54 g.), $[\alpha]_D = + 13°$ (methanol). Two subsequent crystallisations from benzene (50 ml./g; 2 hours at room temperature) gave the dehydroabiethylamine salt of 1-5α-benzyloxymethyl-4β-hydroxycyclopent-2-enyl-1β-acetic acid (42 g.), $[\alpha]_D^{MeOH} = + 10°$. A suspension of this salt in ether-water (2:1) was treated with 1.2 equivalents of 5% potassium hydroxide and extracted with ether. The aqueous layer was then treated with 8N sulphuric acid to pH 1.5, saturated with ammonium sulphate and extracted with chloroform to yield the pure 1-5α-benzyloxymethyl-4β-hydroxy-cyclopent-2-enyl-1β-acetic acid, which showed $[\alpha]_D = -26.5°$; $[\alpha]_{365°} = -78°$ (CHCl$_3$) and $[\alpha]_D = -5.4°$. $[\alpha]_{365°} = -13°$ (MeOH). The mother liquors from the first benzene crystallization were diluted with ether to obtain a benzene-ether ratio of 5:4 and stored for 3 hours at 5°. The precipitated salt (48 g., $[\alpha]_D^{MeOH} = + 27°$) was collected by filtration and recrystallised from benzene-ether (1 g. salt, benzene 20 ml., ether 40 ml.) to yield 44 g. of the dehydroabietylamine salt of d-5β-benzyloxymethyl-4α-hydroxycyclopent-2-enyl-1α-acetic acid, $[\alpha]_D^{MeOH} = + 28.8°$. In a similar way, the 5α-p-methoxybenzyloxymethyl-4β-hydroxy-cyclopent-2-enyl-1β-acetic acid was obtained from the dl-acid.

EXAMPLE 2

An aqueous solution (300 ml.) of the L-ephedrine salt (28 g.) of 5α-methoxymethyl-4β-hydroxy-cyclopent-2-enyl-1β-acetic acid was treated with stirring with potassium iodide (83.2 g.) and iodine (25.44 g.). After 24 hours, the reaction mixture was exhaustively extracted with chloroform. The organic phase was washed with 25% sodium thiosulphate solution saturated with sodium chloride, dried (Na$_2$SO$_4$) and then was evaporated to dryness in vacuo to afford, as an oil, 5α-methoxymethyl-2β,4β-dihydroxy-3α-iodocyclopentyl 1β-acetic acid β-lactone, $[\alpha]_D = + 44.6°$ (C = 2.689 in CHCl$_3$). This compound, in pyridine (44 ml.), was reacted with acetic anhydride (22 ml.) for 2 hours at room temperature. The reaction mixture was poured out in ice-water (200 ml.) and, after acidification to pH 4 with 2N sulphuric acid, was extracted with methylene chloride-ether (1:5, 300 ml.). The organic phase was washed with 2N sulphuric acid (20 ml.), water, 5% sodium bicarbonate and 5% sodium chloride until neutral, dried (Na$_2$SO$_4$) and then was evaporated to dryness to give 5α-methoxymethyl-2β,4β-dihydroxy-3α-iodocyclopentyl-1β-acetic acid-γ-lactone 4-acetate (23.4 g.), m.p. 74.5°–75.5° C. (from ether-hexane) $[\alpha]_D = + 18.7°$, $[\alpha]_{365°} = + 53.3°$ (C = 1,228 in CHCl$_3$).

EXAMPLE 3

Carbon dioxide was bubbled through 5α-benzyloxymethyl-4β-hydroxycyclopent-2-enyl-1β-acetic acid (26.2 g.) in 1N sodium hydroxide until the pH was 8.2, and then an aqueous solution of potassium iodide (63 g.) and iodine (31.75 g.) was added. Working up as described above gave, as an oil, 5α-benzyloxymethyl-2β, 4β-dihydroxy-3α-iodocyclopentyl-1β-acetic acid-γ-lactone, $[\alpha]_D = + 33.5°$ (CHCl$_3$), which was converted to the 4β-acetate, $[\alpha]_D = + 21°$ (CHCl$_3$).

In a similar way, 5α-p-methoxybenzyloxy-4β-hydroxycyclopentyl-1β-acetic acid was converted to 5α-p-methoxybenzyloxymethylcyclopentyl-3α-iodo-2β, 4β-dihydroxy-1β-acetic acid-γ-lactone and its 4-acetate.

EXAMPLE 4

Under a nitrogen atmosphere, 5α-methoxymethyl-2β, 4β-dihydroxy-3α-iodocyclopentyl-1β-acetic acid- γ-lactone 4-acetate (24 g.) in benzene (220 ml.) was treated with tributyl tin hydride (28.18 g.) in benzene (55 ml.); the mixture was heated at 55°; after 3 hours, it was cooled and then diluted with ether (250 ml.). The organic phase was washed with 2.5% sodium bicarbonate (2 × 20 ml.) and 10% sodium chloride until neutral, was dried ($Na_2SO_4$), concentrated in vacuo to 70 ml. and then absorbed on silica (500 g.). Elution with benzene and cyclohexane:ethyl acetate (60:40) gave, as an oil, 5α-methoxymethyl-2β, 4β-dihydroxycyclopentyl-1β-acetic acid-γ-lactone 4-acetate, ($[α]_D$ = +74.3°, $[α]_{365°}$ = + 237° ($CHCl_3$)). This product (12.5 g.) in methanol (250 ml.) was refluxed with an aqueous solution of potassium carbonate (11.05 g.) for 1 hour, cooled to room temperature and treated with 2N sulphuric acid (60 ml.). After 3 hours at room temperature, the salts were filtered and the filtrate was concentrated in vacuo to 150 ml., diluted with saturated sodium chloride solution and was extracted with ethyl acetate. The organic phase was washed to neutrality with 10% sodium chloride, dried and evaporated to dryness to yield, as an oil, 5α-methoxymethyl-2β, 4β-dihydroxycyclopentyl-1β-acetic acid-γ-lactone (10 g.), $[α]_D$ = + 22.5°, $[α]_{365°}$ = +79° (C = 1.34% in $CHCl_3$). This product in pyridine (60 ml.), cooled at 0°, was treated with p-toluenesulphonylchloride (25 g.) in pyridine (30 ml.). After 12 hours at room temperature, the reaction mixture was poured into ice-water (200 g.) and the crystalline precipitate was filtered, washed to neutrality, and dried in vacuo to afford crude 5α-methoxymethyl-2β, 4β-dihydroxycyclopentyl-1β-acetic acid-γ-lactone 4-p-toluenesulphonate (11.6 g.), m.p. 102°-103°. Extraction of the mother liquors with ethyl acetate gave 1.6 g. of the same product. A sample was crystallised from ether hexane and showed m.p. 102.5°-103.2° C.; $[α]_D$ = + 56.1°, $[α]_{365°}$ = + 180° (C = 1.04% in $CHCl_3$).

Using other sulphonyl chlorides the following compounds were prepared:

5α-methoxymethyl-2β, 4β-dihydroxycyclopentyl-1β-acetic acid-γ-lactone 4β-methanesulphonate and 4β-benzenesulphonate.

EXAMPLE 5

Under a nitrogen atmosphere, 5α-methoxymethyl-2β,4β-dihydroxycyclopentan-1β-acetic acid-γ-lactone4-p-toluenesulphonate (10.8 g.), dry potassium acetate (68.2 g.), acetic acid (51.6 ml.) and dry dimethylformamide (80 ml.) were refluxed. After 90 minutes, the reaction mixture was cooled, diluted with water (300 ml.) and extracted with methylene chloride (500 ml. in all). The organic layer was washed with 10% sodium bicarbonate and saturated sodium chloride until neutral and evaporated to dryness in vacuo to afford a crude product (8.2 g.) which was crystallized from hexane-ether to give 5α-methoxymethyl-2β,4α-dihydroxycyclopentyl-1β-acetic acid-γ-lactone 4-acetate (60% yield), m.p. 86°-88°, $[α]_D$ = −12.9°, $[α]_{365°}$ = −18.1° (C = 0.825% in $CHCl_3$). The mother liquors ($\approx$ 3 g.), which were shown by thin layer chromatographic analysis to contain another less polar product, were refluxed with 5% potassium hydroxide in methanol (75 ml.) for 1 hour. The mixture was cooled, treated with 4N sulphuric acid (30 ml.); the precipitated salts were filtered and the filtrate was concentrated in vacuo and diluted with water (75 ml.). The methylene chloride extracts were washed with 5% sodium bicarbonate and with water to neutrality, dried and after evaporation to small volume, the residue was absorbed on a silica (70 g.) column. Elution with methylene chloride gave, from fractions 3-25, 5α-methoxymethyl-2β-hydroxycyclopent-. 3-enyl-1β-acetic acid-γ-lactone (1.05 g.), m.p. 47°-48° C. (from hexane), $[α]_D$ = − 256°, $[α]_{365°}$ = − 892° (C = 0.495% in $CHCl_3$). This compound was not used in the subsequent steps. Further elution with methylene chloride gave, from fractions 38-60, 5α-methoxymethyl-2β,4α-dihydroxycyclopentyl-1β-acetic acid-γ-lactone (1.05 g.), m.p. 105°-106° C. (from ether-hexane), $[α]_D$ = −3.6°, $[α]_{365°}$ = + 12° (C = 0.92% in $CHCl_3$), which was acetylated in pyridine to give the 4α-acetate (1.02 g.; 80% overall yield).

EXAMPLE 6

Under a nitrogen atmosphere, 5α-methoxymethyl-2β,4β-dihydroxy-3α-iodocyclopentyl-1β-acetic acid-γ-lactone (31.2) in benzene (250 ml.) was treated with tributyltinhydride (34 g.) in benzene (70 ml.); the mixture was heated at 55° for 16 hours. After cooling, the mixture was extracted with water (400 ml. in all), the aqueous extracts were saturated with sodium chloride, treated with concentrated hydrochloric acid (5 ml.) and then extracted with chloroform (200 ml.). The chloroform layer was washed to neutrality with 10% sodium chloride, dried and evaporated to dryness in vacuo to afford 5α-methoxymethyl-2β,4β-dihydroxycyclopentyl-1β-acetic acid-γ-lactone (17.2 g.), which was dissolved in pyridine (80 ml.) and treated with p-toluenesulphonylchloride (22 g.) at 0°. After 12 hours at room temperature, the reaction mixture was poured out into ice-water to afford, after working up as described above, 5α-methoxymethyl-2β,4β-dihydroxycyclopentyl-1β-acetic acid-γ-lactone 4β-p-toluenesulphonate (25.84 g.), m.p. 102°-103° C. Under a nitrogen atmosphere, a stirred mixture of this ester (25.8 ), melted potassium acetate (170 g.), acetic acid (127 ml.) and dry dimethylformamide (200 ml.) was refluxed for 1.5 hour, cooled and diluted with water (700 ml.). After several extractions with methylene chloride, the organic layer was washed to neutrality, dried ($Na_2SO_4$) and evaporated to dryness to afford a crude product which was dissolved in 2.5% potassium hydroxide in methanol (200 ml.). The mixture was refluxed for 1 hour, cooled and treated with 4N-sulphuric acid (25 ml.). After 3 hours, the precipitated salts were filtered off and the filtrate was concentrated in vacuo to 80 ml., diluted with water and extracted with methylene chloride. The organic layer was washed to neutrality and evaporated to small volume, and the residue was absorbed on a silica (500 g.) column. Elution with methylene chloride (see Example 5) gave 5α-methoxymethyl-2β-hydroxycyclopent-3-enyl-1β-acetic acid-γ-lactone (3.04 g.) and 5α-methoxymethyl-2β,4α-dihydroxycyclopent-3-enyl-1β-acetic acid-γ-lactone (11.02 g.). The latter compound (9.3 g.) in pyridine was treated with 1.5 equivalents of p-phenylbenzoyl chloride (16.35 g.).

After two days at room temperature, the mixture was poured into ice-water (200 ml.) and extracted with methylene chloride. The organic layer was washed with 2N-sulphuric acid, water, 5% sodium bicarbonate and finally with water till neutral, dried ($Na_2SO_4$) and evaporated to dryness in vacuo. The residue was crystallised from hexane-ether to afford 5α-methoxymethyl-2β,4α-dihydroxycyclopentyl-1β-acetic acid-γ-lactone 4-p-phenylbenzoate (17.4 g.), m.p. 81°-82° C., $[α]_D$ = −76.5°. This compound in methylene chloride (350 ml.), cooled at −50°, was treated under stirring with boron tribromide (36 g.) in methylene chloride (80 ml.).

The reaction mixture was stirred for 15 minutes at 0° and then poured into excess 10% sodium bicarbonate. The organic phase was separated and the aqueous phase re-extracted with methylene chloride. The combined phases were washed with 10% sodium bicarbonate and with water till neutral and the solvent was removed in vacuo to yield the 5α-hydroxymethyl-2β,4α-dihydroxycyclopentyl-1β-acetic acid-γ-lactone 4-p-phenylbenzoate (13.2 g.), m.p. 145°–146°, $[α]_D = -30.5°$.

EXAMPLE 7

A stirred solution of dry pyridine (28 g.) in dry methylene chloride (460 ml.), cooled at 5°, was treated with chromic anhydride (18 g.); the stirring was continued for 15 minutes at 18°–20° to obtain a deep red solution. 5α-Hydroxymethyl-2β,4α-dihydroxycyclopentyl-1β-acetic acid-γ-lactone-4-p-phenylbenzoate (10.56 g.) in methylene chloride was added thereto in a single portion, followed by vigorous stirring for 15 minutes. The organic layer was decanted and the inorganic materials were washed with methylene chloride and benzene and combined with the originally obtained organic layer. After removal of the solvents in vacuo, the residue gave 5-formyl-2β,4α-dihydroxycyclopentyl-1β-acetic acid-γ-lactone-4-p-phenylbenzoate (9.3 g.), m.p. 148°–149°.

A stirred suspension of 80% sodium hydride dispersion in mineral oil (1.2 g.) in benzene (150 ml.) was slowly treated with dimethyl-(2-oxoheptyl)-phosphonate (8.84 g.) in absolute benzene (50 ml.). When the evolution of hydrogen ceased, the solution of the 5-formyl-4-p-phenylbenzoate derivative (9.3 g.) in benzene, described above, was added with vigorous stirring to a suspension in benzene of the sodium salt of the phosphonate. After 20 minutes, saturated sodium dihydrogen phosphate solution was added, the organic layer was separated and washed twice with 10% sodium dihydrogen phosphate. Each of the aqueous wash solutions was re-extracted with benzene and combined with the originally obtained layer.

After removal of the organic solvents in vacuo. the residue was crystallised from ether to afford 5α-(3"-oxo-oct-trans-1"-en-1"-yl)-2β,4α-hydroxycyclopentyl-1β-acetic acid-γ-lactone 4-p-phenylbenzoate (8.3 g.), m.p. 112°–113° $[α]_D = -196°$, $[α]_{365°} = -928°$ (in CHCl$_3$). This compound in dry dimethoxyethane (150 ml.) was added to a 0.07 M-zinc borohydride in ether (630 ml.) over 25 minutes under vigorous stirring. The stirring was continued for another 30 minutes; the excess reagent was then destroyed by cautious addition of moist ether and also of saturated sodium chloride solution. The zinc hydroxide precipitate was dissolved by adding 2N-sulphuric acid, and the organic layer was separated and washed with 2N-sulphuric acid and water to neutrality. Each of the aqueous wash solutions was re-extracted with ether and combined with the organic phase. After drying (Na$_2$SO$_4$) and removal of the solvents in vacuo, the residue was crystallised from isopropyl ether to afford 3.1 g. of 5α-(oct-trans-1"-en-1"-yl)-2β,4α,3"R-trihydroxycyclopentan-1β-acetic acid-γ-lactone 4-p-phenyl-benzoate (less polar epimer), m.p. 141°–142°, $[α]_C = -152°$. The mother liquors were evaporated to dryness in vacuo to afford a residue (4.85 g.) which was absorbed on a silica (2 kg.) column. Elution with ethyl ether-isopropyl ether (1:1), gave the less polar epimer (0.55 g.). Elution with ethyl ether-isopropyl ether (55:45) gave 3.24 g. of 5α-(oct-trans-1"-yl)-2β,4α,3"S-trihydroxycyclopentyl-1β-acetic acid-γ-lactone 4-p-phenylbenzoate (the more polar epimer), m.p. 90°–91° C., $[α]_D = -154°$. This compound (3.01 g.) in methanol (50 ml.) was treated with 14.5 ml. of 20% aqueous sodium carbonate, refluxed for 1 hour, cooled at room temperature and treated with 2N-sulphuric acid (16 ml.).

The mixture was stirred for 3 hours at room temperature. The precipitated salts were filtered and the filtrate was concentrated in vacuo to remove the methanol. The residue was diluted with ethyl acetate and the organic phase was separated. The aqueous layer was repeatedly extracted with ethyl acetate (5 × 25 ml.) and then the organic layers were combined, washed first with saturated sodium bicarbonate to remove the p-phenylbenzoic acid and then with saturated sodium chloride solution till neutral, dried (Na$_2$SO$_4$) and evaporated to dryness in vacuo to afford 5α-(oct-trans-1"-en-1"-yl)-2β,4α,3"S-trihydroxycyclopentyl-γ-lactone (1.8 g.), m.p. 79°–81°, $[α]_D = -36°$. This compound, in benzene (60 ml.), was refluxed with the aqueous azeotrope being removed by a water trap. The cooled solution was treated with dihydropyran (2.8 g.) and p-toluenesulphonic acid (13 mg.) in benzene (4ml.). After 6 hours at room temperature, the benzene layer was washed with 5% sodium bicarbonate and water till neutral, and the solvent was evaporated in vacuo to afford 3.9 g. of a crude product which was absorbed on a silica (100 g.) column. Elution with cyclohexane-ethyl acetate-pyridine (80:20:0.1) afforded, as an oil, pure 5α-(oct-trans-1"-en-1"-yl)-2β,4α,3"S-trihydroxycyclopentyl-1β-acetic acid-γ-lactone 4α,3"S-bis-THP-ether (2.85 g.), $[α]_D = -86°$.

In similar way, using 1,4-diox-2-ene the etherification gave, as an oil, 5α-(oct-trans-1"-en-1"-yl)-2β,4α,3"S-trihydroxycyclopentyl-1β-acetic acid-γ-lactone 4α,3"S-bis-dioxa-1''',4'''-nyl ether $[α]_D = 77°$. Under a nitrogen atmosphere, a stirred solution of the bis-tetrahydropyranylether (2.2 g.) in dry toluene (38 ml.), cooled at −60°, was treated over 10 minutes with 0.5 M-diisobutylaluminium hydride solution (22 ml.). The mixture was stirred for an additional 30 minutes at −60°, and then treated with 7.5 ml. of a 2 M-isopropanol solution in toluene. After 10 minutes, the mixture was warmed up to 0°–2° C., treated with water (1.5 ml.), sodium sulphate (5 g.) and Celite (7 g.), and was then filtered. The filtrate was evaporated to dryness in vacuo to afford, as an oil, 5α-(oct-1"-trans-en-1"-yl)-2β,4α,3"S-trihydroxycyclopentyl-1β-ethanol-γ-lactol-4α,3"-bis-THP-ether (2.15 g.), $[α]_D = -75°$.

Under a nitrogen atmosphere, a suspension of 80% sodium hydride (0.9 g.) in dry dimethylsulphoxide (25 ml.) was heated with stirring at 60° until the evolution of hydrogen ceased. The stirred mixture, cooled to 5°–10°, was treated with triphenyl(4-carboxybutyl)-phosphonium bromide (6.65 g.) in dry DMSO (25 ml.); the deep orange-red solution of the ylid was treated with the lactol (2.15 g.) in DMSO (10 ml.). The mixture was stirred for an additional 3 hours at room temperature, and then diluted with water (60 ml.) under stirring with external cooling at 5°–10° C. The aqueous phase was extracted repeatedly with ether until all the triphenylphosphoxide had been removed, and the combined organic layers were re-extracted with 5% sodium bicarbonate. The pH of the combined aqueous phases was adjusted to 4.5–4.7 with 4N-sulphuric acid and with saturated sodium dihydrogen phosphate solution, followed by extraction with etherpentane (1:1). The organic layers were combined, washed with saturated ammonium sulphate solution, dried (Na$_2$SO$_4$) and evaporated to dryness in vacuo to afford, as an oil, 5-cis-13-trans-8,12-diiso-9β,11α,15S-trihydroxyprostadienoic acid-11,15-bis-THP-ether (2.25 g.), $[\alpha]_D$ = −101°. A stirred solution of this compound (2.24 g.) in acetone (50 ml.), cooled at −20° C., was treated with Jones reagent [4 ml; prepared by adding concentrated sulphuric acid (61 ml.) to chromic anhydride (70 g.) in water (500 ml.)].

The mixture was stirred at −10° to −12° C. for an additional 20 minutes, diluted with benzene (150 ml.), washed with saturated ammonium sulphate solution until neutral, dried ($Na_2SO_4$) and then evaporated to dryness in vacuo to yield, as an oil, 5-cis-13-trans-8,12-diiso-11α,15S-dihydroxy-9-oxoprostadienoic acid-11,15-bis-THP-ether.

This compound in acetone (80 ml.) was treated with 0.1 N-oxalic acid (80 ml.) and the mixture was heated for 6 hours at 36°–38° C. The acetone was then removed in vacuo (the temperature of the water bath was 38°–40° C.) and the residue was extracted repeatedly with ether. The organic extracts were combined, washed to neutrality with saturated ammonium sulphate, dried ($Na_2SO_4$) and evaporated to dryness in vacuo. The residue was absorbed on an acid-washed silica (70 g.) column and eluted with cyclohexaneethyl acetate mixtures.

The eluates from 25/75 cyclohexane-ethylacetate gave, after removal of the solvents in vacuo, the oil 5-cis-13-trans-8,12-diiso-11α,15S-dihydroxy-9-oxoprostadienoic acid [8,12-diiso-$PGE_2$; ent-PG($E_{\beta\beta}$)₂ ] (0.91 g.), $[\alpha]_D$ = +33.2° $[\alpha]_{365°}$ = +323° (C = 1% in ethanol).

EXAMPLE 8

Starting from 5α-(oct-1″-trans-en-1″-yl)-2β,4α,3″R-trihydroxycyclopentyl-1β-acetic acid -γ-lactone 4-p-phenylbenzoate (m.p. 141°–142°, $[\alpha]_D$ = −152°), the less molar epimer, and following the same procedure, we prepared:

(a) 5α-(oct-1″-trans-en-1″-yl)-2β,4α,3″R-trihydroxycyclopentyl-1β-acetic acid γ-lactone, m.p. 78°–79° $[\alpha]_D$ = −57°;

(b) 5α-(oct-1″-trans-en-1″-yl)-2β,4α,3″R-trihydroxycyclopentyl-1β-acetic acid-γ-lactone-4α,3″R-bis-THP-ether, an oil, $[\alpha]_D$ = −3.5°
and its 4α,3″R-bis-dioxa-1‴,4‴-nyl ether, an oil, $[\alpha]_D$ = −12°;

(c) 5α-(oct-1″-trans-en-1″-yl-2β,4α,3″R-trihydroxycyclopentyl-1β-ethanol-γ-lactol-4α,3″-bis-THP-ether, an oil;

(d) 5-cis-13-trans-8,12-diiso-9β,11α,15R-trihydroxyprostadienoic acid-11,15-bis-THP-ether;

(e) 5-cis-13-trans-8,12-diiso-11α,15R-dihydroxy-9-oxoprostadienoic acid-11,15-bis-THP-ether;

(f) 5-cis-13-trans-8,12-diiso-11α,15R-dihydroxy-9-oxoprostadienoic acid [8,12-diiso-15-epi $PGE_2$; ent-PG-($E_{\beta\alpha}$)₂], an oil, $[\alpha]_D$ = +22°, $[\alpha]_{365°}$ = +270° (C = 0.3% in ethanol).

EXAMPLE 9

5α-Methoxymethyl-2β,4α-dihydroxycyclopentyl-1β-acetic acid-γ-lactone 4-acetate (5.6 g.) in dry methylene chloride (85 ml.), cooled to −70°, was treated with a solution (6.6 ml.) of boron tribromide in dry methylene chloride over 10 minutes. After an additional 5 minutes, the mixture was heated at 0°–2° C. and kept there for 90 minutes, and poured into pyridine (50 ml.) in ice-water (200 g.).

The organic phase was separated, washed with water to neutrality, dried ($Na_2SO_4$) and evaporated to dryness. The residue was crystallised from hexane-ether to afford 5α-hydroxymethyl-2β,4α-dihydroxycyclopentyl-1β-acetic acid-γ-lactone 4-acetate (4.5 g.), m.p. 165°–166.5° C, $[\alpha]_D$ = +46.5°.

This compound in 25% DMSO in benzene (100 ml.) was treated with dicyclohexylcarbodiimide (12.48 g.) and pyridine trifluoroacetate (19.25 ml.) in 25% DMSO in benzene [from pyridine (2 ml.) and trifluoroacetic acid (1 ml.) in 25 ml. of 25% DMSO in benzene]. The mixture was stirred for 4 hours at room temperature and then treated with oxalic acid (5.46 g.) in methanol (30 ml.) to destroy the excess carbodiimide. After an additional stirring for 45 minutes, the mixture was diluted with ether (500 ml.) and water (500 ml.). The precipitate was filtered off and the organic layer was separated, washed with 5% sodium bicarbonate and saturated sodium chloride solution to neutrality. The aqueous phases were re-extracted with ether, and the combined organic layers were dried ($Na_2SO_4$) and evaporated to dryness to afford 1.4 g. of crude 5α-formyl-2β,4α-dihydroxycyclopentyl-1β-acetic acid-γ-lactone 4-acetate (1.4 g.). Under a nitrogen atmosphere, a suspension of sodium hydride (0.57 g., 80% in mineral oil) in dry dimethoxyethane, cooled at 0°, was treated with a solution of dimethyl(2-oxoheptyl)phosphonate (4.44 ml.) in dimethoxyethane. The mixture was stirred for an additional hour at room temperature. A solution of the aldehyde in dimethoxyethane was then added under vigorous stirring. After 2 hours, the mixture was diluted with ether-methylene chloride (350 ml; 5:1) and the organic phase was washed to neutrality with saturated sodium chloride solution. Evaporation of the solvents gave 5α-(3″-oxoooct-trans-1″-en-1″-yl)-2β,4α-dihydroxycyclopentyl-1β-acetic acid-γ-lactone 4-acetate (0.5 g.).

0.07 M-zinc borohydride in ether (95 ml.) was treated with stirring dropwise with this lactone (1,256 g.) in dimethoxyethane (16 ml.) over 25 minutes. The reaction mixture was stirred for an additional 30 minutes, the excess reactive was destroyed by adding saturated sodium chloride solution and the zinc hydroxide was dissolved by adding 2N-sulphuric acid. The organic phase was separated, washed to neutrality with saturated ammonium sulphate, and dried ($Na_2SO_4$). After removal of the solvents in vacuo, the residue was adsorbed on a silica (0.5 kg.) column, and elution with cyclohexane-ethyl acetate (80:20) gave 5α-(oct-trans-1″-en-1″-yl-2β,4α,3″R-trihydroxycyclopentyl-1β-acetic acid-γ-lactone 4-acetate (0.62 g.). Elution with cyclohexane-ethylacetate (75:25) gave the 3″S-epimer (0.43 g.).

5α-(Oct-trans-1″-en-1″-yl)-2β,4α,3″S-trihydroxycyclopentyl-1β-acetic acid-γ-lactone 4-acetate in methanol (15.5 ml.) was treated with 20% aqueous sodium carbonate (4.34 ml.) and the mixture was refluxed for 1 hour, cooled at room temperature and then treated with 2N-sulphuric acid (4.6 ml.). After 3 hours, the inorganic materials were filtered and the filtrate was concentrated in vacuo to remove the methanol, diluted with saturated sodium chloride solution and extracted with ethyl acetate (4 × 25 ml.). The organic extracts were combined, washed with 5% sodium bicarbonate and with water to neutrality, dried ($Na_2SO_4$) and evaporated to dryness to afford 5α-(oct-trans-1″-en-1″yl)-2β,4α,3″S-trihydroxycyclopentyl-1β-acetic acid-γ-lactone, m.p. 79°–81°, $[\alpha]_D$ = −36°.

EXAMPLE 10

5α-(Oct-trans-1″-en-1″-yl)-2β,4α,3″R-trihydroxycyclopentyl-1β-acetic acid-γ-lactone 4-acetate (0.535) in dioxan (7 ml.) was treated with 0.4 M-tetrachloroquinone in dioxan (7 ml.). The reaction mixture was heated for 24 hours at 50°–55°, cooled to room temperature and then was diluted with methylene chloride (30 ml.). Following filtration through a short alumina column, the filtrate was evaporated to dryness in vaccuo to afford 5α-(3″-oxoocttrans-1″-en-1″-yl)-2β,4α-dihydroxycyclopentyl-1β-acetic acid-γ-lactone 4-acetate (0.38 g.).

EXAMPLE 11

Under a nitrogen atmosphere, 5α-(oct-t-1″-en-1″-yl)-2β,4α,3″S-trihydroxycyclopentyl-1β-acetic acid-γ-lactone4α,3″S-bisdioxa-1‴,4‴-nylether (4α,3″S-bisdioxanylether) in toluene (650 ml.), cooled at −60°, was treated over 10 minutes with 0.5 M-diisobutylaluminum hydride in toluene (440 ml.), followed by stirring for 80 minutes. 2 M-isopropanol in toluene (150 ml.) was added and the stirring was continued for 10 minutes. The temperature of the reaction vessel was then allowed to rise to about 0°–2° C.

After addition of water (30 ml.), dry sodium sulphate and Celite, the solution was filtered and the eluate was evaporated to dryness in vacuo to afford 5α-(oct-trans-1″-en-1″-yl)-2β,4α,3″S-trihydroxycyclopentyl-1β-ethanol-γ-lactol-4α,3″S-bisdioxanylether (43.9 g.).

Under a nitrogen atmosphere, freshly sublimed potassium tert-butoxide (56.25 g.) in dry (by distillation from calcium hydride) DMSO was added to a stirred solution of this lactol (43.9 g.) and of triphenyl(4-carboxybutyl)-phosphonium bromide (89 g.) in dry DMSO and cooled in an ice-water bath so the temperature of the reaction mixture did not exceed 20° C. The deep red solution was stirred for an additional 12 hours at room temperature, diluted with water (750 ml.) under stirring with external cooling at 5°–10° C.

The aqueous phase was extracted repeatedly with ether (4 litres in all) until all the triphenyl phosphoxide had been removed, and the combined organic layers were re-extracted with 5% sodium bicarbonate. The pH of the combined aqueous phases was adjusted to 4.5–4.7 with 4 N-sulphuric acid (120 ml.) and with saturated sodium dihydrogen phosphate solution, followed by extraction with etherpentane (1:1). The organic layers were combined, washed with saturated ammonium sulphate solution, dried (Na₂SO₄) and evaporated in vacuo to afford 5c-13t-9β,11α,15S-trihydroxy-8,12-diisoprostadienoic acid-11α,15S-bisdioxanylether (46 g.).

EXAMPLE 12

5c-13t-9β,11α,15S-trihydroxy-8,12-diisoprostadienoic acid-11,15S-bisdioxanyl ether (4.6 g.) in isopropanol (200 ml.) was hydrogenated at atmospheric pressure in the presence of 1.15 g. of a 5% palladiumcarbon catalyst, cooling the mixture to below −12° C. After 1.1 equivalents of hydrogen had been adsorbed, the catalyst was filtered off and the solvent removed in vacuo to obtain 13-trans-9β,11α,15S-trihydroxy-8,12-diisoprostenoic acid-11,15-bisdioxanyl ether (4.55 g.) containing 5-6% of 9β,11α,15S-trihydroxy-8,12-diisoprostanoic acid-11,15-bis-dioxanyl ether. In similar way, the reduction of the 11α,15-bis-THP ether afforded 13t-9β,11α,15S-trihydroxy-8,12-diisoprostenoic acid-11,15-bis-THP-ether.

EXAMPLE 13

A prostanoic acid [for example 5-cis-13-trans-9β,11α,15S-trihydroxy-8,12-diiso-prostadienoic acid-11,15-bis-dioxanyl ether (2.2 g.)] in ether was treated with an ethereal solution of diazomethane (1.3 equivalents) at room temperature.

After 3 hours, the mixture was evaporated to dryness in vacuo and the residue was filtered through a short silica column using as eluent cyclohexane-ethyl acetate. In this way the following pure prostanoic acid methyl esters were obtained:

5c-13t-9β,11α,15S-trihydroxy-8,12-diisoprostadienoic acid-11,15-bisdioxanyl ether methylester;
5c-13t-9β,11α,15S-trihydroxy-8,12-diiso-prostadienoic acid-11,15-bis-THP-ether methyl ester;
13t-9β,11α,15S-trihydroxy-8,12-diiso-prostadienoic acid-11,15-bis-dioxanyl ether methylester;
13t-9β,11α,15S-trihydroxy-8,12-diiso-prostadienoic acid-11,15-bis-THP-ether methyl ester.

EXAMPLE 14

A 11,15-bis-ether (a tetrahydropyranyl ether or a dioxa-1′,4′-nyl ether) of a 9β,11α,15S-trihydroxy-8,12-diisoprostadienoic acid (for example 10 g.) in acetone (250 ml.), cooled at −20° C was treated with Jones reagent (10 ml.) over 2 minutes. The reaction mixture was stirred for an additional 20 minutes at −20° to −10°, followed by dilution with benzene (750 ml.). The organic layer was washed many times with 20 ml. of saturated ammonium sulphate till neutral, and dried (Na₂SO₄) followed by removal of the solvent in vacuo to afford the 9-keto derivative (for example, 9.26 g. of 5c-13t-11α, 15S-dihydroxy-9-oxo-8,12-diisoprostadienoic acid-11,15S-bis-dioxanyl ether). Using this procedure, the following compounds were prepared:
13t-11α,15S-dihydroxy-9-oxo-8,12-diisoprostenoic acid-11,15-bis-dioxanyl ether;
13t-11α,15S-dihydroxy-9-oxo-8,12-diisoprostenoic acid-11,15-bis-THP-ether;
5c-13t-11α,15S-dihydroxy-9-oxo-8,12-diisoprostadienoic acid-11,15-bis-dioxanyl ether;
and their methyl esters.

EXAMPLE 15

A methyl ester of a 5c-13t-11α,15S-dihydroxy-9-oxo-8,12-diisoprostadienoic acid-11,15-bis-ether (dioxanyl or THP) (1.14 g.) in 20 ml. of methylene chlorideethanol (1:1), cooled at −15°, was treated with sodium borohydride (52 mg.) followed by stirring for 45 minutes. After addition of acetone (1.2 ml.) and then of saturated sodium dihydrogen phosphate solution (3 ml.), the solvents were concentrated in vacuo to 4 ml. and the residue was diluted with water and extracted with ethyl acetate. The organic layer was separated, dried (NA₂SO₄) and evaporated to dryness in vacuo, to afford an oil (1.12 g.) which was absorbed on a silica column and eluted with cyclohexane-ethyl acetate to afford 0.36 g. of pure 5c-13t-9α,11α,15S-trihydroxy-8,12-diisoprostadienoic acid-11,15-bis-ether (dioxanyl or THP) methyl ester.

This product in tetrahydrofuran (40 ml.) and 0.1 N-oxalic acid (63 ml.) was kept for 8 hours at 38°; the organic solvent was then removed in vacuo. The aqueous phase was extracted with ethyl acetate (75 ml. in all) and the organic layers, after washing to neutrality with saturated ammonium sulphate solution, were dried.

After removal of the solvent, the residue was pruified by silica chromatography, eluting with cyclohexanethyl acetate (1:1), to afford 0.21 g. of 5c-13t-9α,11α-15S-trihydroxy-8,12-diisoprostadienoic acid methyl ester. A solution of this compound in 02 N-sodium hydroxide in methanol was heated at 45° C. for 45 minutes, the excess solvent was removed in vacuo and the residue was diluted with water and extracted with ether. The aqueous phase, acidified with sodium dihydrogen phosphate solution to pH 8, was re-extracted with ether (80 ml. in all).

The organic extracts were combined, washed with sodium chloride solution to neutrality, dried and then evaporated to dryness to afford 5c-13t-9α,11α,15S-trihydroxy-8,12-diisoprostadienoic acid (0.168 g.). In similar way, starting from the corresponding 9-ketones, the following compounds were prepared:

5c-13t-9α,11α,15S-trihydroxy-8,12-diisoprostadienoic acid-11,15-bis-THP-ether methyl ester;
5c-13t-9α,11α,15S-trihydroxy-8,12-diisoprostadienoic acid-11,15-bis-dioxanyl ether methyl ester;
13t-9α,11α,15S-trihydroxy-8,12-diisoprostenoic acid-11,15-bis-THP-ether methyl ester;
13t-9α,11α,15S-trihydroxy-8,12-diisoprostenoic acid-11,15-bis-dioxanyl ether methyl ester;
13t-9α,11α,15S-trihydroxy-8,12-diisoprostenoic acid methyl ester;
13t-9α,11α,15S-trihydroxy-8,12-diisoprostenoic acid.

EXAMPLE 16

A 11α,15S-bis-ether (dioxanyl or THP ether) of 5c-13t-9β,11α,15S-trihydroxy-8,12-diisoprostadienoic acid (0.6 g.) in tetrahydrofuran and 0.25 N-cirtic acid (100 ml.; 1:1) was heated at 38° C. for 8 hours; the organic solvents were removed in vacuo (the temperature of external bath (40°). The aqueous phase was extracted with ether (50 ml. in all); the organic extracts were combined, washed with saturated sodium chloride solution to neutrality, and dried (Na$_2$SO$_4$). After removal of solvent, the residue was purified by column chromatography on acid-washed silica (20 g.), using as eluent ethyl acetate, to obtain 5c-13t-9β,11α,15S-trihydroxy-8,12-diisoprostadienoic acid (0.27 g.).

Using the same procedure, starting from the corresponding 11,15-bis-ether, the following compounds were obtained:
13t-9β,11α,15S-trihydroxy-8,12-diisoprostenoic acid;
13t-9β,11α,15S-trihydroxy-8,12-diisoprostenoic acid methyl ester;
5c-13t-9β,11α,15S-trihydroxy-8,12-diisoprostadienoic acid methyl ester;
5c-13t-9β,11α,15R-trihydroxy-8,12-diisoprostadienoic acid;
5c-13t-11α,15S-dihydroxy-9-oxo-8,12-diisoprostadienoic acid methyl ester;
13t-11α,15S-dihydroxy-9-oxo-8,12-diisoprostenoic acid methyl ester.

EXAMPLE 17

5α-Benzyloxymethyl-2β,4β-dihydroxy-3α-iodocyclopentyl-1β-acetic acid-γ-lactone 4-acetate (0.96 g.), hexamethylphosphonamide (7.8 ml.) and sodium cyanoborohydride (0.4 g.) were heated, under stirring, for 2 ½ hours at 70°, followed by cooling to room temperature. Excess reagent was destroyed by adding ice-water. The mixture was diluted with water (20 ml.) and extracted with cyclohexane. The combined extracts were washed to neutrality with saturated sodium chloride solution, dried and evaporated to dryness to afford 5α-benzyloxymethyl-2β,4β-dihydroxycyclopentyl-1β-acetic acid-γ-lactone 4-acetate (0.58 g.), [α]$_D$ = +50.5° (CHCl$_3$).

EXAMPLE 18

Under a nitrogen atmosphere, a stirred mixture of chromous acetate (1.7 g.) thioethanol (1 ml.) and DMSO (40 ml.) was treated dropwise with 5α-p-methoxybenzyloxymethyl-2β,4β-dihydroxy-3α-iodocyclopentyl-1β-acetic acid-γ-lactone 4-acetate (0.83 g.) in DMSO (20 ml.). The reaction mixture was stirred for an additional 1½ hours at room temperature, and then diluted with water (40 ml.) and extracted with ether (2 × 40 ml.). The combined extracts were washed with 5% sodium bicarbonate (10 ml.) and water to neutrality, dried and evaporated in vacuo to afford 5α-p-methoxybenzyloxymethyl-2β,4β-dihydroxycyclopentyl-1β-acetic acid-γ-lactone 4-acetate (0.51 g.).

EXAMPLE 19

5α-Benzyloxymethyl-2β,4β-dihydroxycyclopentyl-1β-acetic acid-γ-lactone 4-acetate (25 g.) in methanol (500 ml.) was refluxed with 22% aqueous potassium carbonate (100 ml.) for 1 hour. After cooling to room temperature, the mixture, acidified by adding 4 N-sulphuric acid (60 ml.), was stirred for an additional 2 hours, followed by filtration of the precipitated salts. After removal of the excess methanol in vacuo, the aqueous phase was extracted with methylene chloride to afford 5α-benzyloxymethyl-2β,4β-dihydroxycyclopentyl-1β-acetic acid-γ-lactone (2 g.), [α]$_D$ = + 7° (CHCl$_3$). Starting from the above 4-acetate and using the same procedure, 5α-p-methoxybenzyloxymethyl-2β,4β-dihydroxycyclopentyl-1β-acetic acid-γ-lactone was obtained. By reacting these 4β-hydroxy derivatives with a sulphonyl chloride in pyridine the following compounds were prepared.

5α-benzyloxymethyl-2β,4β-dihydroxycyclopentyl-1β-acetic acid-γ-lactone-4-p-toluenesulphonate; m.p. 92°-94° C. (from ether), [α]$_D$ = +37.5°;
5α-benzyloxymethyl-2β,4β-dihydroxycyclopentyl-1β-acetic acid-γ-lactone-4-methanesulphonate;
5α-benzyloxymethyl-2β,4β-dihydroxycyclopentyl-1β-acetic acid-γ-lactone-4-benzenesulphonate;
5α-p-methoxybenzyloxymethyl-2β,4β-dihydroxycyclopentyl-1β-acetic acid-γ-lactone-4-p-toluenesulphonate;
5α-p-methoxybenzyloxymethyl-2β,4β-dihydroxycyclopentyl-1β-acetic acid-γ-lactone-4-methanesulphonate;
5α-p-methoxybenzyloxymethyl-2β,4β-dihydroxycyclopentyl-1β-acetic acid-γ-lactone-4-benzenesulphonate.

EXAMPLE 20

5α-p-Methoxybenzyloxymethyl-2β,4β-dihydroxycyclopentyl-1β-acetic acid-γ-lactone-4-benzenesulphonate (0.8 g.) hexamethylphosphoric triamide (10 ml.), potassium propionate (5 g.) and propionic acid (3.3 ml.) were heated for 4 hours at 100° under a nitrogen atmosphere. The reaction mixture was diluted with water and extracted with cyclohexane. The combined extracts were washed with water to neutrality dried and evaporated in vacuo to afford, after crystallisation from hexane-methylene chloride, 5α-p-methoxybenzyloxymethyl-2β,4α-dihydroxycyclopentyl-1β-acetic acid-γ-lactone-4-propionate.

EXAMPLE 21

5α-Benzyloxymethyl-2β,4β-dihydroxycyclopentyl-1β-acetic acid-γ-lactone-4-methanesulphonate (2.28) potassium formate (12.6 g.), formic acid (7.48 ml.) and dimethylformamide (45 ml.) were refluxed for 2 hours, cooled at room temperature and then diluted with water (45 ml.).

The methylene chloride extracts (90 ml. in all) were combined, washed to neutrality, dried and evaporated to dryness in vacuo. The residue was refluxed with 5% methanolic potassium hydroxide (40 ml.) for 1 hour as described above, and, after acidification with 2 N-sulphuric acid, the methanol was removed in vacuo. Extraction with methylene chloride gave 5α-benzyloxymethyl-2β,4α-dihydroxycyclopentyl-1β-acetic acid-γ-lactone, m.p. 78°–79°, $[\alpha]_D = -21.5°$, $[\alpha]_{365°} = -39.1°$ (CHCl$_3$) and 5α-benzyloxy-methyl-2β-ol-cyclopent-3-enyl-1γ-acetic acid-γ-lactone as a oil, $[\alpha]_D = -171°$; $[\alpha]_{365°} = -374°$, (CHCl$_3$).

These compounds were separated by column chromatography on silica using methylene chloride as eluent to afford the inverted 2β,4α-diol derivative (1.4 g.). 5α-Benzyloxymethyl-2β,4α-dihydroxycyclopentyl-1β-acetic acid-γ-lactone (1.4 g.), p-phenylbenzoyl chloride (1.5 g.) and pyridine (7 ml.) were stirred for 2 days at room temperature, diluted with water and the crystalline precipitate, removed by filtration, was dissolved in methylene chloride. The organic solution was washed with 5% sodium bicarbonate (6 × 9 ml.) and with water to neutrality; after removal of the solvent, the residue was crystallised from hexane to afford 5α-benzyloxymethyl-2β,4α-dihydroxycyclopentyl-1β-acetic acid-γ-lactone-4-p-phenylbenzoate, m.p. 93.5°–94.5°, $[\alpha]_D = -72°$, $[\alpha]_{365°} = -154°$, (CHCl$_3$).

In similar way, 5α-p-methoxybenzyloxymethyl-2β,4α-dihydroxycyclopentyl-1β-acetic acid-γ-lactone-4-p-phenylbenzoate was prepared.

EXAMPLE 22

Starting from a 5α-alkoxymethyl-2β,4α-dihydroxycyclopentyl-1β-acetic acid-γ-lactone, wherein the alkoxy group is a methoxy, benzyloxy and p-methoxybenzyloxy group, esterification in pyridine with 1.3 molar equivalents of both acetic, acetic-formic or propionic anhydride and benzoyl or p-phenylbenzoyl chloride, gave the 4α-formate, acetate, m.p. 76°–77°, $[\alpha]_D = -29.5°$, $[\alpha]_{365°} = -74°$(CHCl$_3$), propionate, benzoate and p-phenylbenzoate.

EXAMPLE 23

5α-Benzyloxymethyl-2β,4α-dihydroxycyclopentyl-1β-acetic acid-γ-lactone-4-propionte (3.2 g.), tritylfluoborate (3.96 g.) and dry methylene chloride (45 ml.) were stirred for 4 hours at room temperature.

The reaction mixture was washed with 5% sodium bicarbonate and water to neutrality and dried and then, after concentration to 10 ml., the residue was absorbed on silica (50 g.) and eluted with chloroform to obtain 5α-hydroxymethyl-2β,4α-dihydroxycyclopentyl-1β-acetic acid-γ-lactone-4-propionate.

EXAMPLE 24

5α-Benzyloxymethyl-2β,4α-dihydroxycyclopentyl-1β-acetic acid-γ-lactone-4-p-phenylbenzoate (2.65 g.), ethyl acetate (25 ml.), ethanol (12.5 ml.) and concentrated hydrochloric acid (0.12 ml.) were hydrogenated with stirring for 5 hours under a 34 p.s.i. hydrogen pressure in the presence of 10% palladium-carbon. The catalyst was filtered off, the filtrate was diluted with chloroform and washed with saturated sodium chloride solution to neutrality. After drying (Na$_2$SO$_4$) and removal of solvent under reduced pressure, the residue was crystallised from ether to yield 5α-hydroxymethyl-2β,4α-dihydroxcyclopentyl-1β-acetic acid-β-lactone-4-p-phenylbenzoate (1.92 g.), m.p. 145°–146° C., $[\alpha]_D = -30.5°$.

EXAMPLE 25

A stirred solution of 5α-benzyloxymethyl-2β,4α-dihydroxycyclopentyl-1β-acetic acid-γ-lactone-4-p-phenylbenzoate (0.89 g.) in dry methylene chloride (30 ml.), cooled at −60°, was treated with boron tribromide (1.5 g.) in methylene chloride (6 ml.). The mixture was kept for 5 minutes at −60° and then for 10 minutes at 0° C. It was then poured into excess 10% sodium carbonate. The organic layer was separated, washed to neutrality and dried, and, after removal of the solvent, the residue was purified by column chromatography on silica, eluting with chloroform, to afford 5α-hydroxymethyl-2β,4α-dihydroxycyclopentyl-1β-acetic acid-γ-lactone-4-p-phenylbenzoate (0.61 g.)

EXAMPLE 26

Under a nitrogen atmosphere, a suspension of 0.3 g. of sodium hydride (80% dispersion in mineral oil) in dimethoxyethane was treated dropwise with 3(d,l)-methyl-2-oxo-heptyl-dimethoxyphosphonate (2.36 g.) in dimethoxyethane. The mixture was stirred for one additional hour at room temperature, and then treated with 5α-formylcyclopentyl-2β,4α-dihydroxy-1β-acetic acid-γ-lactone-4-p-phenylbenzoate (3.45 g.) in dimethoxyethane.

After an additional stirring for 20 minutes, the reaction mixture was diluted with ether (5 volumes), washed with saturated sodium chloride solution and dried (Na$_2$SO$_4$). The solvents were removed in vacuo, and the residue was purified by column chromatography on silica (160 g.). Elution with cyclohexane-ether (40:60) gave dl-5α-(4''-methyl-3oxooct-1''-en-1''-yl)-2β,4α-dihydroxycylopentyl-1β-acetic acid-γ-lactone-4-p-phenylbenzoate (3.2 g.).

EXAMPLE 27

Reacting 5α-formyl-2β,4α-dihydroxycyclopentyl-1β-acetic acid-γ-lactone-4-p-phenylbenzoate in benzene (Example 7) or dimethoxyethane (Example 26) with the sodium salt of (1-methyl-2-oxoheptyl)dimethoxyphosphonate or (2-oxo-octyl)-dimethoxyphosphonate gave:

(1) 5α-(3-oxo-non-trans-1''-en-1''-yl)-2β,4α-dihydroxycyclopentyl-1β-acetic acid-γ-lactone-4-p-phenylbenzoate;

(2) 5α-(2''-methyl-3''-oxooct-trans-1''-en-1''yl)-2β,4α-dihydroxycyclopentyl-1β-acetic acid-γ-lactone-4-p-phenylbenzoate.

EXAMPLE 28

0.07 M-zinc borohydride in ether was treated with stirring with product (1) (14.9 g.) from Example 27 in dry dimethoxyethane. After stirring for 1 additional hour, the excess reagent was destroyed by added saturated sodium chloride solution, followed by adding 4 N-sulphuric acid to dissolve the precipitated inorganic materials. The organic phase was separated, washed to neutrality with a saturated ammonium sulphate solution, dried and then was evaporated to dryness in vacuo. Chromatographic separation on silica using ethyl ether:isopropyl ether (1:1) as eluent gave pure 5α-(non-trans-1″-en-1″-yl)-2β,4α,3″S-trihydroxycyclopentyl-1β-acetic acid-γ-lactone-4-p-phenylbenzoate (more polar) (7.45 g.). The less polar epimeric alcohol (3″R, 6.3 g.) in dioxan was treated with 2,3-dichloro-5,6-dicyano-p-benzoquinone for 26 hours at 58°. The reaction mixture was diluted with methylene chloride (300 ml.) and filtered through a short alumina (50 g.) column. Further elution with methylene chloride gave the starting trans-enone-lactone (5.1 g.).

EXAMPLE 29

Using the trans-enone-lactones prepared in Examples 26 and 27, in the procedure of Example 28 the following were prepared:

5α-(non-trans-1″-en-1″-yl)-cyclopentyl-2β,4α,3″R-trihydroxy-1β-acetic acid-γ-lactone-4-p-phenylbenzoate;

5α-(2″-methyloct-trans-1″en-1″-yl)-2β,4α,3″S-trihydroxycyclopentyl-1β-acetic acid-γ-lactone-4-p-phenylbenzoate and its 3″R-epimer;

5α-(4″-methyloct-trans-1″-en-1″-yl)-2β,4α,3″S-trihydroxycyclopentyl-1β-acetic acid-γ-lactone-4-p-phenylbenzoate and its 3″R-epimer.

EXAMPLE 30

A p-phenylbenzoate ester (2 g.), prepared in Examples 28, 29, in 10% aqueous methanolic potassium carbonate was refluxed for 1 hour, cooled and then was acidified to pH 2 with 2 N-sulphuric acid. After 2 hours, the excess methanol was removed in vacuo and the aqueous layer, diluted with saturated sodium chloride solution (15 ml.) was extracted with ether-methylene chloride (4:1). The organic layer was repeatedly washed with 5% sodium bicarbonate to remove the p-phenylbenzoic acid and with water to neutrality, and dried (Na$_2$SO$_4$). Removal of the solvents in vacuo gave the following:

5α(non-trans-1″-en-1″-yl)-2β,4α,3″S-trihydroxycyclopentyl-1β-acetic acid-γ-lactone and its 3″R-epimer;

5α-(2″-methyloct-trans-1″-en-1″-yl)-2β,4α,3″S-trihydroxycyclopentyl-1β-acetic acid-γ-lactone and its 3″R-epimer;

5α-(4″-methyloct-trans-1″-en-1″-yl)-2β,4α,3″S-trihydroxypentyl-1β-acetic acid-γ-lactone and its 3″R-epimer.

EXAMPLE 31

The diol derivative (3.6 g.) of the last Example in dry benzene (30 ml.) was reacted at room temperature with 1,4diox-2-ene (2.4 ml.) and dry p-toluenesulphonic acid (20 mg.) in benzene. After 4 hours at room temperature, the reaction mixture was washed with 3% potassium carbonate and with water to neutrality, and dried (Na$_2$SO$_4$) to afford, after removal of the solvents, the following bis-dioxa-1‴, 4‴-nylethers (bis-dioxanyl ether):

5α-(non-trans-1″-en-1″yl)-2β,4α,3S″-trihydroxycyclopentyl-1β-acetic acid-γ-lactone-4,3″S-bis-dioxanyl ether;

5α-(non-trans-1″-en-1″-yl)-2β,4α,3″R-trihydroxycyclopentyl-1β-acetic acid-γ-lactone-4,3″R-bis-dioxanyl ether;

5α-(2″-methyloct-trans-1″-en-1″-yl)-2β,4α,3″S-trihydroxycyclopentyl-1β-acetic acid-γ-lactone-4,3″S-bis-dioxanyl ether;

5α-(2″-methyloct-trans-1″-en-1″yl)-2β,4α,3″R-trihydroxycyclopentyl-1β-acetic acid-γ-lactone-4,3″R-bis-dioxanyl ether;

5α-(4″-methyloct-trans-1″-en-1″-yl)-2β,4α,3″S-trihydroxycyclopentyl-1β-acetic acid-γ-lactone-4,3″S-bis-dioxanyl ether;

5α-(4″-methyloct-trans-1″-en-1″-yl)-2β,4α,3″R-trihydroxycyclopentyl-1β-acetic acid-γlactone-4,3″R-bis-dioxanyl ether.

EXAMPLE 32

Using 2,3-dihydropyran in the procedure of Example 31, the following tetrahydropyranyl ether derivatives (bis-THP-ethers) were obtained:

5α-(non-trans-1″-en-1″-yl)-2β,4α,3″S-trihydroxycyclopentyl1β-acetic acidγ-lactone-4-3″S-bis-THP-ether;

5α-(non-trans-1″-en-1″-yl)-2β,4α,3″R-trihydroxycyclopentyl-1β-acetic acidγ-lactone-4,3″R-bis-THP-ether;

5β-(2″-methyloct-trans-1″-en-1″-yl)-2β,4α,3″S-trihydroxycyclopentyl-1β-acetic acidγ-lactone-4,3″S-bis-THP-ether;

5α-(2″-methyloct-trans-1″-en-1″-yl)-2β,4α,3″R-trihydroxycyclopentyl-1β-acetic acid-γ-lactone-4,3″R-bis-THP-ether;

5α-(4″-methyloct-trans-1″-en-1″-yl)-2β,4α,3″S-trihydroxycyclpentyl-1β-acetic acid-γ-lactone-4,3″S-bis-THP-ether;

5α-(4″-methyloct-trans-1″-en-1″-yl)-2β,4α,3″R-trihydroxycyclopentyl-1β-acetic acid-γ-lactone-4,3″R-bis-THP-ether.

EXAMPLE 33

Under a nitrogen atmosphere, a stirred solution of 5α-(non-trans-1″-en-1″-yl)2β,4α,3″S-trihydroxycyclopentyl-1β-acetic acid-γ-lactone-4α,3″-bis-dioxanyl ether (4.5 g.) in dry toluene (105 ml.) was cooled at −65° and treated with 70% sodium-bis-(2-methoxyethoxy)aluminium hydride in benzene (3 ml.) diluted with 10 ml. of dry toluene.

The reaction mixture was stirred for an additional 2 hours at −65° to −60°, and 2 N-isopropanol in toluene (15 ml.) was added, followed by warming up to +2° C. After addition of water (3 ml.) and dry sodium sulphate, the mixture was filtered on Celite; the filtrate gave, after removal of the solvents, 5α-(non-trans-1″-en-1″-yl)-2β,4α,3″S-trihydroxycyclopentyl-1β-ethanol-γ-ethanol-γ-lactol-4α,3″S-bis-dioxanyl ether (4.45 g.).

EXAMPLE 34

Under a nitrogen atmosphere, a stirred solution of 5α-(2″-methyloct-trans-1″-en-1″-yl)-2β,4α,3″S-trihydroxycyclopentyl-1β-acetic acid-γ-lactone-4α,3″-bis-THP-ether (4.4 g.) in dry toluene (90 ml.) was cooled at −65° and treated with 0.5 M-DIBA in toluene (44 ml.), followed by stirring for 30 minutes. The reaction mixture was treated with 2 M-isopropanol solution in toluene (15 ml.), warmed to 2° C. and then treated with water and with sodium sulphate to afford, after filtration and concentrated under reduced pressure, 5α-(2″-methyloct-trans-1″-en-1″-yl)-2β,4α,3″-trihydroxycyclopentyl-1β-ethanol-γ-lactol-4α,3″S-bis-THP-ether (4.38 g.).

EXAMPLE 35

The reductions with DIBA and with sodium-bis-(2-methoxy ethoxy) aluminium hydride of the bis ethers, prepared in Examples 31 and 32, gave the bis ether (4,3''-bis-dioxanyl-ether and 4,3''-bis-THP-ether) derivatives of the following lactols:

5α-(non-trans-1''-en-1''-yl)-2β,4α,3''S-trihydroxycyclopentyl-1β-ethanol-γ-lactol;

5α-(non-trans-1''-en-1''-yl)-2β,4α,3''R-trihydroxycyclopentyl-1β-ethanol-γ-lactol;

5α-(2''-methyloct-trans-1''-en-1''-yl)-2β,4α,3''S-trihydroxycyclopentyl-1β-ethanol-γ-lactol;

5α-(2''-methyloct-1''-en-1''-yl)-2β,4α,3''R-trihydroxycyclopentyl-1β-ethanol-γ-lactol;

5α-(4''-methyloct-1''-en-1''-yl)-2α,4α,3''S-trihydroxycyclopentyl-1β-ethanol-γ-lactol;

5α-(4''-methyloct-1''-en-1''-yl)-2α,4α3''R-trihydroxycyclopentyl-1β-ethanol-γ-lactol.

EXAMPLE 36

Under a nitrogen atmosphere, freshly sublimed potassium tert-butoxide (5.62 g) in dimethylsulphoxide (25 ml) was added dropwise to a stirred mixture of (β-carboxymethoxyethyl)triphenylphosphonium bromide (8.9 g) and a 4α,3''S-bis-ether of the 5α-(non-trans-1''-en-1''-yl)-2β,4α,3''S-trihydroxycyclopentyl-1β-ethanol-γ-lactol (4.5 g) in DMSO (25 ml), with external cooling by an ice-water bath. After additional stirring for 6 hours at room temperature, the mixture was diluted with water (75 ml), and extracted with ether to remove the triphenylphosphoxide. The organic extracts were washed with 5% sodium bicarbonate, and the aqueous phases t-ωcombined, acidified to pH 4.6 – 4.8 with 2N-sulphuric acid and then re-extracted with etherpentane (1:1 to afford 11α,15S-bis ether of the 5c-13S-ω-homo-9β,11α,15S-trihydroxy-8,12-diiso-3-oxaprostadienoic acid (5.2 g.). This compound (2.3 g.) in ether was reacted with ethereal diazomethane (1.3 mol equivalents) to afford, after removal of the solvent in vacuo after 3 hours, the corresponding methyl ester. A solution of this acid or its methyl ester (1 g) was dissolved in acetone —0.1N oxalic acid (100 ml; 1:1) and heated for 8 hours at 38°, followed by removal of the organic solvent in vacuo. The aqueous phase was extracted with ether, washed to neutrality with saturated ammonium sulphate solution and dried. After removal of the solvent, the residue was purified on an acid-washed silica column using cyclohexane-ethyl acetate as eluent to afford 5c-13t-ω-homo-9β,11α,15S-trihydroxy-8,12-diiso-3-oxaprostadienoic acid.

EXAMPLE 37

Using the procedure of Example 36, the lactol derivatives of Examples 7, 8, 33 and 35, were reacted with the Wittig reagent derived from the (β-carboxymethoxyethyl)triphenylphosphonium bromide, to afford the following bis ethers (11α,15-dioxanyl or 11α,15-THP) prostadienoic acids:

5c-13t-9β,11α,15S-trihydroxy-3-oxa-8,12-diisoprostadienoic acid;

5c-13t-9β,11α,15R-trihydroxy-3-oxa-8,12-diisoprostadienoic acid;

5c-13t-9β-11α,15S-trihydroxy-14-methyl-3-oxa-8,12-diisoprostadienoic acid;

5c-13t-9β,11α,15R-trihydroxy-14-methyl-3-oxa-8,12-diisoprostadienoic acid;

5c-13t-9β,11α,15S-trihydroxy-16-methyl-3-oxa-8,12-diisoprostadienoic acid;

5c-13t-9β,11α,15R-trihydroxy-16-methyl-3-oxa-8,12-diisoprostadienoic acid;

5c-13t-ω-homo-9β-11α,15S-trihydroxy-3-oxa-8,12-diisoprostadienoic acid;

5c-13t-ω-homo-9β,11α,15R-trihydroxy-3-oxa-8,12-diisoprostadienoic acid, which were optionally converted into their methyl esters and then deetherified.

EXAMPLE 38

Using (4-carboxybutyl)triphenylphosphonium bromide in the procedure of Example 37 gave:

5c-13t-9β,11α,15S-trihydroxy-14-methyl-8,12-diisoprostadienoic acid;

5c-13t-9β,11α,15S-trihydroxy-16-methyl-8,12-diisoprostadienoic acid;

5c-13t-ω-homo-9β,11α,15S-trihydroxy-8,12-diisoprostadienoic-acid and their methyl esters.

Using (β-carboxymethylthioethyl)triphenylphosphonium bromide in the procedure of Example 37 gave:

5c-13t-9β,11α,15S-trihydroxy-3-thia-8,12-diisoprostadienoic acid;

5c-13t-9β,11α,15S-trihydroxy-14-methyl-3-thia-8,12-diisoprostadienoic acid;

5c-13t-9β,11α,15S-trihydroxy-16-methyl-3-thia-8,12-diisoprostadienoic acid;

5c-13t-ω-homo-9β,11α,15S-trihydroxy-3-thia-8,12-diisoprostadienoic acid.

Using (4-carboxy-but-trans-3-entyl)triphenylphosphonium bromide in the procedure of Example 37 gave:

2t-5c-13t-9β,11α,15S-trihydroxy-8,12-diisoprostatrienoic acid;

2t-5c-13t-9β,11α,15S-trihydroxy-ω-homo-8,12-diisoprostatrienoic acid.

EXAMPLE 39

ω-Homo-9β,11α,15S-trihydroxy-5c-13t-8,12-diisoprostadienoic acid 11α,15S-bis-dioxanyl ether methyl ester (4.6 g) in methanol (200 ml) was hydrogenated at —10° C in the presence of 1.16 g of 5% palladiumcarbon at atmospheric pressure until 1.12 equivalents of hydrogen had been adsorbed. The catalyst was filtered off and the mixture was evaporated to dryness to afford 13t-ω-homo-9β,11α,15S-trihydroxy-8,12-diisoprostenoic acid-11α,15S-bis-dioxanyl ether methyl ester.

Deetherification with acetone-0.1N oxalic acid and subsequent hydrolysis with 0.1N methanolic potassium hydroxide gave the free prostenoic acid which was purified by acid washed silica column chromatography, using cyclohexane-ethyl acetate (10:90) as eluent, to yield 13t-ω-homo-9β,11α,15S-trihydroxy-8,12-diisoprostenoic acid (1.8 g.).

In similar way, starting from the corresponding prostadienoic acids, the following were obtained:

13t-3-oxa-9β,11α,15S-trihydroxy-8,12-diisoprostenoic acid;

13t-3-oxa-ω-homo-9β,11α,15S-trihydroxy-8,12-diisoprostenoic acid;

13t-14-methyl-9β,11α,15S-trihydroxy-8,12-diisoprostenoic acid.

EXAMPLE 40

A stirred solution of a 11,15-bis-ether (11,15-dioxanyl or 11,15 THP) of ω-homo-9β,11α,15S-trihydroxy-5c-13t-8,12-diisoprostadienoic acid (1.2g.) in acetone (30 ml), cooled at —10°, was treated with Jones reagent (1.2 ml.). After 20 minutes at —20°, the mixture was diluted with benzene (85 ml), washed to neutrality with saturated ammonium sulphate solution, dried and evaporated to dryness.

The ω-homo-9-oxo-11α,15S-dihydroxy-5c,13t-8,12-diisoprostadienoic acid-11, 15-bis ether (1.1 g) so obtained was dissolved in acetone (40 ml.) and 0.1N oxalic acid (40 ml.) and the mixture was heated for 4 hours at 38°. The acetone was removed in vacuo and the aqueous phase was extracted with ether, washed with saturated ammonium sulphate solution to neutrality and dried ($Na_2SO_4$). Removal of the solvent in vacuo, followed by chromatographic purification on an acid washed silica column using, as eluent, cyclohexane-ethyl acetate (40:60) gave 5c-13t-ω-homo-11α,15S-dihydroxy-9-oxo-8,12-diisoprostadienoic acid. (0.43 g.).

EXAMPLE 41

Starting from the corresponding 9β,11α,15S-trihydroxy-8,12-diisoprostanoic acid-11,15-bis-ethers (dioxanyl ether or THP-ether) or their methyl esters, oxication with Jones reagent, followed by deetherification gave the following:

ω-homo-5c-13t-11α,15S-dihydroxy-9-oxo-8,12-diisoprostadienoic acid;

ω-homo-13t-11α,15S-dihydroxy-9-oxo-8,12-diisoprostenoic acid;

ω-homo-5c-13t-11α,15S-dihydroxy-9oxo-3-oxa-8,12-diisoprostadienoic acid;

5c-13-t-11α,15S-dihydroxy-9-oxo-3-oxa-8,12-diisoprostadienoic acid;

14-methyl-5c-13t-11α,15S-dihydroxy-9-oxo-3-oxa-8,12-diisoprostadienoic acid;

16-methyl-5c-13t-11α,15S-dihydroxy-9-oxo-3-oxa-8,12-diisoprostadienoic acid;

16-methyl-5c-13t-11α,15S-dihydroxy-9-oxo-8,12-diisoprostadienoic acid, 14-methyl-5c-13t-11α,15S-dihydroxy-9-oxo-8,12-diisoprostadienoic acid;

2t-5c-13t-11α,15S-dihydroxy-9-oxo-8,12-diisoprostatrienoic acid;

ω-homo-2t-5c-13t-11α,15S-dihydroxy-9-oxo-8,12-diisoprostatrienoic acid and their methyl esters.

EXAMPLE 42

Starting from the 9-oxo-bis ethers of Example 41, reduction with sodium borohydride followed by deetherification and working up as described in Example 15, gave:

ω-homo-5c-13t-9α,11α,15S-trihydroxy-8,12-diisoprostadienoic acid;

ω-homo-13t-9α,11α-15S-trihydroxy-8,12-diisoprostenoic acid;

ω-homo-5c-13t-9α,11α,15S-trihydroxy-3-oxa-8,12-diisoprostadienoic acid;

5c-13t-9α,11α,15S-trihydroxy-3-oxa-8,12-diisoprostadienoic acid;

14-methyl-5c,13t-9α,11α,15S-trihydroxy-3-oxa-8,12-diisoprostadienoic acid;

16-methyl-5c-13t-9α,11α,15S-trihydroxy-3-oxa-8,12-diisoprostadienoic acid;

16-methyl-5c-13t-9α,11α,15S-trihydroxy-8,12-diisoprostadienoic acid;

14-methyl-5c-13t-9α,11α,15S-trihydroxy-8,12-diisoprostadienoic acid;

2t-5c-13t-9α,11α,15S-trihydroxy-8,12-diisoprostatrienoic acid;

ω-homo-2t-5c-13t-9α,11α,15S-trihydroxy-8,12-diisoprostatrienoic acid;

and their methyl esters.

EXAMPLE 43

5c,13t-9β,11α,15S-Trihydroxy-8,12-diisoprostadienoic acid-11α,15S-bis-THP-ether methyl ester (2.1 g) in pyridine (3 ml), cooled at 0°, was treated with p-toluenesulphonylchloride (1.05 g) and the mixture was stirred for 12 hours at room temperature, followed by dilution with water (10 ml). The aqueous phase was extracted with ether, washed with 2N-sulphuric acid, water, 5% sodium bicarbonate, and water to neutrality to afford, after drying ($Na_2SO_4$) and concentration under reduced pressure, 5c,13t-9β,11α,15S-trihydroxy-8,12-diisoprostadienoic acid-11α,15S-bis-THP-ether-9β-p-toluenesulphonate methyl ester (2.12 g.). Under a nitrogen atmosphere this compound in dry dimethylformamide (20 ml) was heated with melted potassium acetate (1.6 g) and refluxed with stirring for 45 minutes. The cooled reaction mixture was diluted with water (30 ml), and extracted with ethermethylene chloride (5:1, 80 ml in all); the residue (1.52 g after drying and concentration under reduced pressure, d,dissolved in 5% methanolic potassium hydroxide. After refluxing for 1 hour, the mixture was concentrated in vacuo to remove the methanol and diluted with water. The aqueous phase was extracted with ether to remove non-acidic materials, and was acidifed to pH 4.8; it was then extracted with ethyl acetate to yield, after drying and concentration under reduced pressure, 1.18 g. of a mixture of the 11α,15S-bis-THP-ether derivatives of 5c, 13t,9α,11d-15S-trihydroxy-8,12-diisoprostadienoic acid and of 5c,13t,11α,15-dihydroxy-8,12-diiso-S-prosta-5,9,13-trienoic acid, which was dissolved in acetone - 0.1N-oxalic acid (80 ml.; 1:1) and heated at 38° for 12 hours, followed by removal of acetone in vacuo and by extraction of the aqueous phase with ether.

After drying and evaporation of the solvent, the residue (1.1 g) was absorbed on an acid-washed silica (75 g) column. Elution with cyclohexane-ethyl acetate (40:60) gave 5c,13t-11α,15S-dihydroxy-8,12-diisoprosta-5,9,13-trienoic acid (270 mg).

Elution then with cyclohexane-ethylacetate (10:90) gave 5c,13t-9α,11α,15S-trihydroxy-8,12-diisoprostadienoic acid (355 mg.)

EXAMPLE 44

Starting from the corresponding 9β,11α,15S-trihydroxy-8,12-diisoprostenoic acid 11,15-bis ether methyl ester reaction with a sulphonyl chloride according to the procedure of Example 43 gave the following:

13t-9β,11α,15S-trihydroxy-8,12-diisoprostenoic acid-9-methane sulphonate;

5c,13t-9β,11α,15S-trihydroxy-ω-homo-8,12-diisoprostadienoic acid-9-p-toluenesulphonate;

13t-9β,11α,15S-trihydroxy-ω-homo-8,12-diisoprostenoic acid-9-benzenesulphonate;

5c,13t-9β,11α,15S-trihydroxy-3-oxa-8,12-diisoprostadienoic acid-9-p-toluenesulphonate;

5c,13t-9β,11α,15S-trihydroxy-3-oxa-ω-homo-8,12-diisoprostadienoic acid-9-p-toluenesulphonate;

5c,13t-9β,11α,15S-trihydroxy-3-thia-8,12-diisoprostadienoic acid-9-methanesulphonate;

5c,13t-9β,11α,15S-trihydroxy-3-thia-ω-homo-8,12-diisoprostadienoic acid-9-methanesulphonate.

EXAMPLE 45

Under a nitrogen atmosphere, 5c,13t-9β,11α,15S-trihydroxy-3-oxa-8,12-diisoprostadienoic acid-9-p-toluenesulphonate (0.5 g) in DMSO (5 ml) was treated with dry potassium formate (0.3 g), and the stirred mixture was heated at 80° for 6 hours. After dilution with water (10 ml), the aqueous phase was extracted with methylene chloride to afford a mixture of the Δ$^{9(10)}$-9-ene and the 9α-formate ester. By the procedure of Example 43, this mixture was converted by saponification and deetherification to the free acids which were separated by column chromatography on acid-washed silica to afford 5c-13t-11α,15S-dihydroxy-3-oxa-8,12-diisoprosta-5,9,13-trienoic acid (35 mg.,) and 5c-13t-9α,-11α,15S-trihydroxy-3-oxa-8,12-diisoprostadienoic acid (49 mg.).

EXAMPLE 46

Using the 9β-sulphonate esters described in Example 44 and the procedures of Examples 43 and 45, the following were obtained:

13t-9α,11α,15S-trihydroxy-8,12-diisoprostenoic acid;
5c,13t-9α,11α,15S-trihydroxy-ω-homo-8,12-diisoprostadienoic acid;
13t-9α,11α,15S-trihydroxy-ω-homo-8,12-diisoprostenoic acid;
5c,15t-9α,11α,15S-trihydroxy-3-oxa-ω-homo-8,12-diisoprostadienoic acid;
5c,13t-9α,11α,15S-trihydroxy-3-thia-8,12-diisoprostadienoic acid;
5c,13t-9α,11α,15S-trihydroxy-3-thia-ω-homo-8,12-diisoprostadienoic acid;
13t-11α,15S-dihydroxy-8,12-diisoprosta-9,13-dienoic acid
5c,13t-11α,15S-dihydroxy-ω-homo-8,12-diisoprosta-5,9,13-trienoic acid;
13t-11α,15S-dihydroxy-ω-homo-8,12-diisoprosta-9,13-dienoic acid;
5c,13t-11α,15S-dihydroxy-3-oxa-ω-homo-8,12-diisoprosta-5,9,13-trienoic acid;
5c,13t-11α,15S-dihydroxy-3-thia-8,12-diisoprosta-5,9,13-trienoic acid;
5c,13t-11α,15S-dihydroxy-3-thia-ω-homo-8,12-diisoprosta-5,9,13-trienoic acid.

We claim:
1. Compounds of general formula (I):

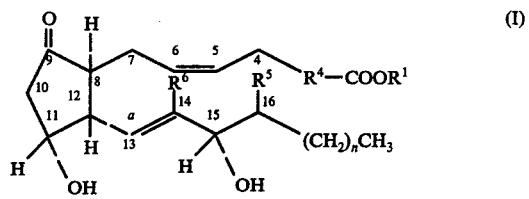

wherein $R^1$ is a hydrogen atom, a cation of a pharmaceutically acceptable base or a $C_{1-12}$ alkyl group; $R^4$ is —$CH_2CH_2$—; n is 3 or 4; each of $R^5$ and $R^6$, which may be the same or different, is a hydrogen atom or a $C_{1-4}$ alkyl group; and double bond a is a trans-double bond.

2. Compound according to claim 1 wherein $R^6$ is a hydrogen atom.
3. 5c,13t-11α,15S-dihydroxy-9-oxo-8,12-diisoprostadienoic acid, as claimed in claim 1.
4. 5c,13t-11α,15S-dihydroxy-9-oxo-ω-homo-8,12-diisoprostadienoic acid, as claimed in claim 1.
5. 5c,13t-11α,15S-dihydroxy-9-oxo-16-methyl-3-oxa-8,12-diisoprostadienoic acid, as claimed in claim 1.
6. 5c,13t-11α,15S-dihydroxy-9-oxo-16-methyl-8,12-diisoprostadienoic acid, as claimed in claim 1.
7. 5c,13t-11α,15S-dihydroxy-9-oxo-14-methyl-8,12-diisoprostadienoic acid, as claimed in claim 1.
8. 5c,13t-11α,15S-dihydroxy-9-oxo-ω-homo-3-oxa-8,12-diisoprostadienoic acid.
9. 5c,13t-11α,15S-dihydroxy-9-oxo-3-oxa-8,12-diisoprostadienoic acid.
10. 5c,13t-11α,15S-dihydroxy-9-oxo-14methyl-3-oxa-8,12-diisoprostadienoic acid.
11. 2t,5c,13t-11α,15S-dihydroxy-9-oxo-8,12-diisoprostatrienoic acid.
12. 2t,5c,13t-11α,15S-dihydroxy-9-oxo-ω-homo-8,12-diisoprostatrienoic acid.
13. 5c,13t-9α,11α,15S-trihydroxy-3-thia-ω-homo-8,12-diisoprostadienoic acid.

* * * * *